(12) United States Patent
Gouda et al.

(10) Patent No.: US 11,054,417 B2
(45) Date of Patent: Jul. 6, 2021

(54) FLUORESCENT NANOPARTICLES FOR BIOMOLECULAR STAINING AND MANUFACTURING METHOD FOR SAME

(71) Applicant: Konica Minolta, Inc., Tokyo (JP)

(72) Inventors: Hideki Gouda, Tokyo (JP); Masaru Takahashi, Musashino (JP); Kensaku Takanashi, Hino (JP); Fuminori Okada, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 931 days.

(21) Appl. No.: 14/896,831

(22) PCT Filed: Apr. 23, 2014

(86) PCT No.: PCT/JP2014/061407
§ 371 (c)(1),
(2) Date: Dec. 8, 2015

(87) PCT Pub. No.: WO2014/203614
PCT Pub. Date: Dec. 24, 2014

(65) Prior Publication Data
US 2016/0178621 A1    Jun. 23, 2016

(30) Foreign Application Priority Data

Jun. 19, 2013 (JP) ............................. JP2013-128412

(51) Int. Cl.
| | | |
|---|---|---|
| *G01N 33/543* | (2006.01) |
| *B82Y 5/00* | (2011.01) |
| *B82Y 15/00* | (2011.01) |
| *C09B 67/00* | (2006.01) |
| *C09B 67/08* | (2006.01) |
| *B82Y 30/00* | (2011.01) |
| *B82Y 40/00* | (2011.01) |

(52) U.S. Cl.
CPC .......... *G01N 33/54346* (2013.01); *B82Y 5/00* (2013.01); *B82Y 15/00* (2013.01); *C09B 67/0013* (2013.01); *C09B 68/41* (2013.01); *C09B 68/444* (2013.01); *B82Y 30/00* (2013.01); *B82Y 40/00* (2013.01)

(58) Field of Classification Search
CPC .... G01N 33/54346; B82Y 5/00; B82Y 15/00; B82Y 30/00; B82Y 40/00; C09B 68/444; C09B 67/0013; C09B 68/41
See application file for complete search history.

(56) References Cited

U.S. PATENT DOCUMENTS

| 4,326,008 A | 4/1982 | Rembaum |
| 5,326,692 A | 7/1994 | Brinkley et al. |
| 2002/0149656 A1 | 10/2002 | Nohr |
| 2010/0298536 A1* | 11/2010 | Park ................... A61K 49/0041 530/326 |
| 2010/0322864 A1* | 12/2010 | Marcus .................... B82Y 5/00 424/9.3 |
| 2012/0190049 A1 | 7/2012 | Zhang |
| 2013/0011864 A1 | 1/2013 | Wang et al. |
| 2013/0039848 A1 | 2/2013 | Bradbury et al. |
| 2013/0157287 A1* | 6/2013 | Takanashi .......... G01N 21/6428 435/7.1 |

FOREIGN PATENT DOCUMENTS

| CN | 102134253 A | 7/2011 | |
| CN | 102713612 A | 10/2012 | |
| JP | 2008543982 | 12/2008 | |
| WO | 2006/041613 A2 | 4/2006 | |
| WO | 2010082681 | 7/2010 | |
| WO | WO-2012029752 A1 * | 3/2012 | ............. G01N 33/48 |
| WO | 2012/175665 A1 | 12/2012 | |
| WO | 2013035703 | 3/2013 | |
| WO | 2013059528 | 4/2013 | |

OTHER PUBLICATIONS

Notification of Reasons for Rejection dated Sep. 19, 2017 from corresponding Japanese Application No. JP 2015-522629 and English translation.
Extended European Search Report dated Jan. 4, 2017 from the corresponding European Application No./Patent No. 14813697.1-1454 / 3012632 PCT/JP2014061407; Total of 11 pages.
Non Patent Literature by Harlad F. Krung, "Nanomaterial, Dokumnentkennung RD-14-02336", Römpp Online, Version 3.26, Apr. 1, 2009, XP55035458, URL:http://www.roepp.com/prod/roempp.php.
Non Patent Literature by Bagwe R P et al., "Surface Modification of 1-15 Silica Nanoparticles to Reduce Aggregation and Nonspecific Binding", Langmuir, American Chemical Society, US, vol. 22, No. 9, Mar. 31, 2006, pp. 4537-4362, XP009070408, ISSN: 0743-7463.
International Search Report (with English Translation).
Written Opinion of the International Searching Authority (with English Translation).

(Continued)

*Primary Examiner* — Tracy Vivlemore
*Assistant Examiner* — Nam P Nguyen
(74) *Attorney, Agent, or Firm* — Lucas & Mercanti, LLP

(57) ABSTRACT

For fluorescent nanoparticles having a zeta potential of −10 mV to −60 mV at pH 7.0 or a zeta potential of 0 mV to −10 mV in a buffer of pH 6.0 to 8.0, an appropriate electrical repulsive force can be generated between biomolecules that are generally negatively charged and the fluorescent nanoparticles. As a result, non-specific binding between the fluorescent nanoparticles and the biomolecules is suppressed and the fluorescent nanoparticles are specifically bound to a biomolecule to be stained through interaction stronger than the electrical repulsive force, so that the visibility of the specific biomolecule to be stained can be improved. Further, since an appropriate electrical repulsive force is also generated between the fluorescent nanoparticles themselves, aggregation of the fluorescent nanoparticles can be inhibited and the dispersibility in a staining solution can thereby be maintained.

9 Claims, 1 Drawing Sheet

(56) References Cited

OTHER PUBLICATIONS

Non Patent Literature by Harald F. Krug, "Nanomaterial, Dokumentkennung RD-14-02336", Römpp Online, Version 3.26, Apr. 1, 2009, XP55035458, URL:http://www.roepp.com/prod/roempp.php.

Non Patent Literature by Bagwe R P et al., "Surface Modification of Silica Nanoparticles to Reduce Aggregation and Nonspecific Binding", Langmuir, American Chemical Society, US, vol. 22, No. 9, Mar. 31, 2006, pp. 4357-4362, XP009070408, ISSN: 0743-7463.

Office Action dated Apr. 17, 2017 from corresponding Chinese Application No. 201480034863.9 and English translation; Applicant: Konica Minolta, Inc.; Total of 19 pages.

Chinese Office Action dated Jul. 20, 2016 from the corresponding Chinese Application; Patent Application No. 201480034863.9; Applicant: Konica Minolta Inc.; English translation of Chinese Office Action; Total of 21 pages.

EPO, Office Action for the corresponding European patent application No. 14813697.1, dated Jul. 24, 2019 (7 pages).

\* cited by examiner (A)
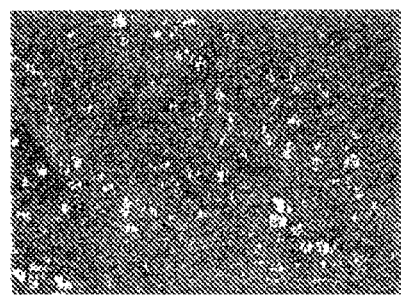
(B)
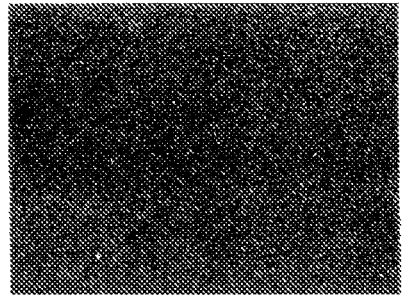
(C)
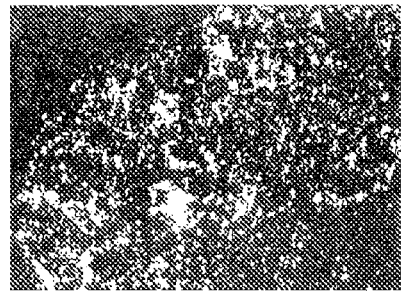
(D)
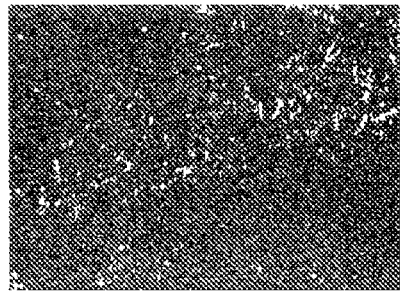

FLUORESCENT NANOPARTICLES FOR BIOMOLECULAR STAINING AND MANUFACTURING METHOD FOR SAME

CROSS REFERENCE TO RELATED APPLICATION

This Application is a 371 of PCT/JP2014/061407 filed on Apr. 23, 2014 which, in turn, claimed the priority of Japanese Patent Application No. JP2013-128412 filed on Jun. 19, 2013, both applications are incorporated herein by reference.

TECHNICAL FIELD

The present invention relates to fluorescent nanoparticles for biomolecular staining and a method of producing the same.

BACKGROUND ART

In pathological diagnosis, immunological observation in which molecular target staining called immunostaining is performed for verifying the expression of molecular information of a specimen and functional abnormalities such as abnormal expression of a gene or a protein are diagnosed is performed. For immunostaining, for example, a dye staining method using an enzyme (e.g., DAB staining) is employed. In staining with an enzyme label such as DAB staining, however, since the depth of color is largely variable depending on the environmental conditions such as temperature and time, there is a problem that estimation of the actual amount of an antibody based on the depth of color is difficult. Therefore, for immunological observation in pathological diagnosis, fluorescent labeling using a fluorescent label is also performed as an alternative to staining with an enzyme label. This method characteristically has superior quantitative capability than DAB staining. In fluorescent labeling, the amount of the target antigen is determined by staining the antigen with an antibody conjugated with a fluorescent dye and observing the stained antigen.

As materials used for fluorescent labeling, staining solutions that contain fluorescent nanoparticles obtained by allowing streptavidin as a biomolecule-recognizing molecule to directly bind to melamine resin particles are known (see, for example, Patent Documents 1 and 2). These fluorescent nanoparticles are used for detection of biomolecules.

PRIOR ART REFERENCES

Patent Documents

[Patent Document 1] Japanese Translated PCT Patent Application Laid-open No. 2008-543982
[Patent Document 2] WO2013/035703

SUMMARY OF THE INVENTION

Problems to be Solved by the Invention

However, when immunostaining is performed using the fluorescent nanoparticles of Patent Document 1 or 2, regardless of the amount of antigen on the target tissue, there is a problem that the fluorescent nanoparticles non-specifically bind to cell nuclei and the like. Especially, when the fluorescent nanoparticles are used at a high concentration in order to perform highly sensitive immunostaining, such non-specific binding is likely to occur.

An object of the present invention is to provide: fluorescent nanoparticles for biomolecular staining, whose non-specific binding to biomolecules other than a biomolecule to be stained can be suppressed; and a method of producing the same.

Solution to Problem

In order to achieve at least one of the above-described objects, the fluorescent nanoparticles reflecting one aspect of the present invention are fluorescent nanoparticles for staining a biomolecule, the fluorescent nanoparticles comprising: dye resin particles having a fluorescent dye; and a biomolecule-recognizing molecule specifically binding to the biomolecule to be stained, wherein the fluorescent nanoparticles have a zeta potential of −10 mV to −60 mV in water of pH 7.0.

In order to achieve at least one of the above-described objects, the fluorescent nanoparticles reflecting one aspect of the present invention are fluorescent nanoparticles for fluorescently staining a biomolecule, the fluorescent nanoparticles comprising: dye resin particles having a fluorescent dye; and a biomolecule-recognizing molecule specifically binding to the biomolecule to be stained, wherein the fluorescent nanoparticles have a zeta potential in a range of 0 mV to −10 mV in a buffer of pH 6.0 to 8.0.

In order to achieve at least one of the above-described objects, the method of producing the above-described fluorescent nanoparticles that reflects one aspect of the present invention is a method of producing fluorescent nanoparticles, the method comprising the step of chemically modifying the surfaces of dye resin particles having a fluorescent dye embedded therein or immobilized thereon so as to impart the dye resin particles with a zeta potential that allows the resulting fluorescent nanoparticles as a whole to have a zeta potential of −10 mV to −60 mV in water of pH 7.0.

In order to achieve at least one of the above-described objects, the method of producing the above-described fluorescent nanoparticles that reflects one aspect of the present invention is a method of producing fluorescent nanoparticles, the method comprising the step of chemically modifying the surfaces of dye resin particles having a fluorescent dye embedded therein or immobilized thereon so as to impart the dye resin particles with a zeta potential that allows the resulting fluorescent nanoparticles as a whole to have a zeta potential of 0 mV to −10 mV in a buffer of pH 6.0 to 8.0.

Advantageous Effects of Invention

According to the present invention, by controlling the zeta potential of fluorescent nanoparticles to be in a specific negative value range, an appropriate electrical repulsive force can be generated between biomolecules that are generally negatively charged and the fluorescent nanoparticles. As a result, non-specific binding between the fluorescent nanoparticles and the biomolecules is suppressed and the fluorescent nanoparticles are specifically bound to a biomolecule to be stained through interaction stronger than the electrical repulsive force, so that the visibility of the specific biomolecule to be stained can be improved. Further, since an appropriate electrical repulsive force is also generated between the fluorescent nanoparticles themselves, aggregation of the fluorescent nanoparticles can be suppressed and the dispersibility in a staining solution can thereby be maintained.

BRIEF DESCRIPTION OF DRAWINGS

FIG. 1(A) is an image of a test for evaluating non-specific binding using the fluorescent nanoparticles of Comparative Example 1. A large number of bright spots are confirmed, indicating that a large amount of the fluorescent nanoparticles are non-specifically bound to cell nuclei. FIG. 1(B) is an image showing the result of a test for evaluating non-specific binding where the fluorescent nanoparticles of Example 1 were used. No bright spot is confirmed, indicating that non-specific binding of the fluorescent nanoparticles to cell nuclei and the whole tissue is suppressed. FIG. 1(C) is an immunostained image obtained by using the fluorescent nanoparticles of Example 7. It can be confirmed that the fluorescent nanoparticles are appropriately bound to the biomolecules of interest (HER2) while non-specific binding thereof to cell nuclei is suppressed. FIG. 1(D) is an immunostained image obtained by using the fluorescent nanoparticles of Example 6. As in FIG. 1(C), it can be confirmed that the fluorescent nanoparticles are appropriately bound to the biomolecules of interest (HER2) while non-specific binding thereof to cell nuclei is suppressed; however, the number of bright spots is slightly less than that of FIG. 1(C).

MODE FOR CARRYING OUT THE INVENTION

The fluorescent nanoparticles according to the present invention are fluorescent nanoparticles for fluorescently staining a biomolecule, the fluorescent nanoparticles comprising: dye resin particles having a fluorescent dye; and a biomolecule-recognizing molecule specifically binding to the biomolecule to be stained, wherein the fluorescent nanoparticles have a zeta potential of −10 mV to −60 mV in water of pH 7.0.

Other fluorescent nanoparticles according to the present invention are fluorescent nanoparticles for fluorescently staining a biomolecule, the fluorescent nanoparticles comprising: dye resin particles having a fluorescent dye; and a biomolecule-recognizing molecule specifically binding to the biomolecule to be stained, wherein the fluorescent nanoparticles have a zeta potential in a range of 0 mV to −10 mV in a buffer of pH 6.0 to 8.0.

(Fluorescent Nanoparticles)

As described above, the fluorescent nanoparticles used in the present invention comprises: dye resin particles that contain a fluorescent dye for staining and have a chemically modified surface; and a biomolecule-recognizing molecule that molecularly recognizes a biomolecule to be stained and specifically binds thereto, and the fluorescent nanoparticles have a negative zeta potential in a specific range at a pH of staining environment.

The term "biomolecule" encompasses cell organelles such as cell nucleus, ribosome and Golgi apparatus as well as various proteins existing intracellularly or on the cell surface. These biomolecules are usually negatively charged in a neutral pH range because of the phosphate groups of nucleic acid (nucleotide) and charged functional groups contained in the side chains of amino acids. Therefore, the fluorescent nanoparticles having a negative zeta potential and such negatively charged biomolecules electrically repel each other, making non-specific binding therebetween unlikely to occur.

Meanwhile, the fluorescent nanoparticles comprise a biomolecule-recognizing molecule specifically binding to a biomolecule to be stained; therefore, the fluorescent nanoparticles are capable of binding with the biomolecule to be stained through interaction far stronger than the above-described electrical repulsive force.

Accordingly, by controlling the zeta potential of the fluorescent nanoparticles in water of pH 7.0 to be in a specific negative range (−10 mV to −60 mV), the fluorescent nanoparticles can be specifically bound to the biomolecule to be stained while non-specific binding of the fluorescent nanoparticles to other biomolecules is suppressed, so that the visibility of fluorescent staining can be improved. Further, the visibility of fluorescent staining can also be improved by controlling the zeta potential in a buffer of pH 6.0 to pH 8.0 to be in a specific negative range (0 mV to −10 mV).

In order to obtain fluorescent nanoparticles that "have a negative zeta potential in a specific range at a pH of staining environment" as described above, the zeta potential of the fluorescent nanoparticles used in the present invention is set to be in a range of −10 mV to −60 mV under a neutral environment, that is, in water of pH 7.0, or to be 0 mV to −10 mV under an environment of a pH buffer such as PBS where pH is 6.0 to 8.0. The buffer can be, for example, at least one selected from the group consisting of phosphate buffered saline (PBS), Tris-HCl buffers and phosphate buffers (excluding PBS).

The fluorescent nanoparticles having a zeta potential in the above-described range are suitable for the use in a pH environment where biomolecular staining is performed, for example, in a pH range of 6.0 to 8.0, preferably 6.9 to 7.6.

When the zeta potential of the fluorescent nanoparticles in water of pH 7.0 is higher than −10 mV, the repulsive force acting between the fluorescent nanoparticles and biomolecules not to be stained (for example, cell nuclei) is weak and non-specific binding therebetween cannot be sufficiently suppressed; therefore, the visibility-improving effect is poor. In addition, since the electrical repulsive force acting between the fluorescent nanoparticles themselves is also weak, the reagent dispersibility is also poor. When the zeta potential of the fluorescent nanoparticles in water of pH 7.0 is lower than −60 mV, adsorption of the fluorescent nanoparticles to the whole tissue (indicated by the number of bright spots) occurs excessively due to, for example, non-specific binding to positively charged biomolecules, so that the visibility-improving effect is also poor in this case.

Meanwhile, when the zeta potential of the fluorescent nanoparticles in a buffer of pH 6.0 to pH 8.0 is outside the range of 0 mV to −10 mV, staining cannot sufficiently yield bright spots. The zeta potential of the fluorescent nanoparticles can be measured using a common zeta potential-measuring device (such as "Zetasizer Nano" manufactured by Malvern Instruments Ltd.).

Usually, there are various kinds of biomolecules that are not the staining subject and may induce non-specific binding, and the degree of their negative charge varies depending on the type of the biomolecule and the pH environment; therefore, it is appropriate to control the zeta potential of the fluorescent nanoparticles in accordance with the staining target (such as a tissue section) such that non-specific binding is inhibited and the visibility-improving effect can be attained at the highest level possible. For example, it is preferred to control the zeta potential of the fluorescent nanoparticles in such a manner that non-specific binding thereof is best suppressed in the relationship with cell nuclei where, among those biomolecules that are not the staining target, non-specific binding is particularly problematic.

As shown in the below-described addition step of the method of producing fluorescent nanoparticles, it is preferred that the zeta potential of the fluorescent nanoparticles in water of pH 7.0 or that of the fluorescent nanoparticles in a buffer of pH 6.0 to pH 8.0 be set in the above-described range by chemical modification of adding a compound capable of controlling the surface zeta potential to the surfaces of the dye resin particles. In this case, the zeta potential of the fluorescent nanoparticles in water of pH 7.0 or that of the fluorescent nanoparticles in a buffer of pH 6.0 to pH 8.0 is comprehensively controlled based on the electric charges, molecular sizes and the like of not only the dye resin particles and biomolecule-recognizing molecule but also reagents used for the chemical modification such as an amino group-introducing reagent and a PEGylation reagent.

However, the present invention is not restricted to such an embodiment, and it is not required to employ such chemical modification as long as the zeta potential of the fluorescent nanoparticles in water of pH 7.0 or that of the fluorescent nanoparticles in a buffer of pH 6.0 to pH 8.0 can be set in the above-described range solely by the dye resin particles and biomolecule-recognizing molecule.

Meanwhile, the zeta potential of the fluorescent nanoparticles in a buffer of pH 6.0 to pH 8.0 may also be comprehensively controlled to be in a range of 0 mV to −10 mV by incorporating a prescribed amount of one or more other compounds capable of controlling the zeta potential, such as a protein (e.g., BSA), a surfactant (e.g., Tween 20 (registered trademark)) and/or a preservative (e.g., sodium azide), into the buffer. However, it is not required to use such a compound as long as the above-described zeta potential is set in a range of 0 mV to −10 mV.

<Dye Resin Particles>

The dye resin particles, one of the elements constituting the fluorescent nanoparticles of the present invention, are resin particles that comprise a fluorescent dye embedded therein or immobilized on the surface and have a diameter in the order of nanometers.

As a resin that mainly constitutes the dye resin particles, the following thermoplastic resin or thermosetting resin can be used. As a thermoplastic resin, for example, polystyrene, polyacrylonitrile, polyfuran, or a resin equivalent thereof can be suitably used. As a thermosetting resin, for example, polyxylene, polylactic acid, glycidyl methacrylate, polymelamine, polyurea, polybenzoguanamine, polyamide, phenol resin, polysaccharide, or a resin equivalent thereof can be suitably used. A thermosetting resin, particularly a melamine resin is preferred because elution of the dye embedded in the dye resin can also be suppressed by processes such as dehydration, clearing and mounting where an organic solvent such as xylene is used.

It is required that the dye resin particles comprise, on the surfaces thereof: at least a functional group for directly or indirectly binding the biomolecule-recognizing molecule; and, usually, a functional group for binding a compound (chemical modifier) used for controlling the zeta potential of the fluorescent nanoparticles in water of pH 7.0 or in a buffer of pH 6.0 to pH 8.0.

As these prescribed functional groups, the same functional groups as those used for allowing various biomolecules to bind with each other in the technical field to which the present invention belongs can be utilized; however, for example, an epoxy group and an amino group are preferred.

The functional group for binding the biomolecule-recognizing molecule and the functional group for binding a compound (chemical modifier) used for controlling the zeta potential may be the same or different.

The method of preparing the dye resin particles having the above-described prescribed functional groups is not particularly restricted and, for example, a method in which, as a monomer(s) for synthesizing the thermoplastic resin or thermosetting resin constituting the dye resin particles, a (co)monomer(s) already having the prescribed functional groups in a side chain is/are (co)polymerized, or a method in which the thermoplastic resin or the thermosetting resin is synthesized and then the functional groups of the resin monomer unit constituting the resin are treated with a reagent and thereby converted into the prescribed functional groups, can be employed.

For the production of thermoplastic dye resin particles, for example, an embodiment of producing dye resin particles composed of a polystyrene-based resin that have an epoxy group on the surface by copolymerizing styrene and glycidyl methacrylate as monomers, an embodiment of producing dye resin particles composed of a polystyrene-based resin that have carboxylic acid and/or sulfonic acid on the surface by copolymerizing styrene along with styrenecarboxylic acid and/or styrenesulfonic acid, or an embodiment of producing dye resin particles composed of a polystyrene-based resin that have an amino group on the surface by copolymerizing styrene with aminosulfonic acid can be adopted. The epoxy group of glycidyl methacrylate can also be converted into an amino group by a prescribed treatment.

Meanwhile, for the production of thermosetting dye resin particles, for example, an embodiment of producing dye resin particles composed of a melamine-based resin that have an amino group on the surface by copolymerizing a melamine resin material (such as MX035 manufactured by Sanwa Chemical Co., Ltd.) as a monomer can be adopted.

(Fluorescent Dye)

In the formation of dye resin particles by polymerizing the above-described resin monomer(s) while incorporating a fluorescent dye, as the fluorescent dye to be embedded in the resulting particles or immobilized on the particle surfaces, for example, the below-described rhodamine-based dye molecules, BODIPY-based dye molecules, squarylium-based dye molecules, aromatic hydrocarbon-based dye molecules or a combination thereof can be used.

Fluorescent dyes such as rhodamine-based dye molecules are preferred because of their relatively high light resistance. Thereamong, perylene, pyrene and perylene diimide that belong to aromatic hydrocarbon-based dye molecules are preferred.

Specific examples of the rhodamine-based dye molecules include 5-carboxy-rhodamine, 6-carboxy-rhodamine, 5,6-dicarboxy-rhodamine, rhodamine 6G, tetramethyl rhodamine, X-rhodamine, Texas Red, Spectrum Red, LD700 PERCHLORATE, and derivatives thereof.

Specific examples of the BODIPY-based dye molecules include BODIPY FL, BODIPY TMR, BODIPY 493/503, BODIPY 530/550, BODIPY 558/568, BODIPY 564/570, BODIPY 576/589, BODIPY 581/591, BODIPY 630/650 and BODIPY 650/665 (all of which are manufactured by Invitrogen), and derivatives thereof.

Specific examples of the squarylium-based dye molecules include SRfluor 680-carboxylate, 1,3-bis[4-(dimethylamino)-2-hydroxyphenyl]-2,4-dihydroxycyclobutenediylium dihydroxide, bis,1,3-bis[4-(dimethylamino)phenyl]-2,4-dihydroxycyclobutene diylium dihydroxide, bis,2-(4-(diethylamino)-2-hydroxyphenyl)-4-(4-(diethyliminio)-2-hydroxycyclohexa-2,5-dienylidene)-3-oxocyclobut-1-enolate, 2-(4-(dibutylamino)-2-hydroxyphenyl)-4-(4-(dibutyliminio)-2-hydroxycyclohexa-2,5-dienylidene)-3-oxocyclobut-1-enolate, 2-(8-hydroxy-1,1,7,7-tetramethyl-1,2,3,5,6,7-hexahydropyrido[3,2,1-ij]quinolin-9-yl)-4-(8-hydroxy-1,1,7,7-tetramethyl-2,3, 6,7-tetrahydro-1H-pyrido

[3,2,1-ij]quinolinium-9(5H)-ylidene)-3-oxocyclobut-1-enolate, and derivatives thereof.

Specific examples of the aromatic hydrocarbon-based dye molecules include N,N-bis-(2,6-diisopropylphenyl)-1,6,7, 12-(4-tert-butylphenoxy)-perylene-3,4,9,10-tetracarbonacid diimide, N,N'-bis(2,6-diisopropylphenyl)-1,6,7,12-tetra-phenoxyperylene-3,4:9,10-tetracarboxdiimide, N,N'-bis(2, 6-diisopropylphenyl)perylene-3,4,9,10-bis(dicarbimide), 16,N,N'-bis(2,6-dimethylphenyl)perylene-3,4,9,10-tetracarboxylic diimide, 4,4'-[(8,16-dihydro-8,16-dioxodibenzo[a,j] perylene-2,10-diyl)dioxy]dibutyric acid, 2,10-dihydroxy-dibenzo[a,j]perylene-8,16-dione, 2,10-bis(3-aminopropoxy) dibenzo[a,j]perylene-8,16-dione, 3,3'-[(8,16-dihydro-8,16-dioxodibenzo[a,j]perylene-2, 10-diyl)dioxy]dipropylamine, 17-bis(octyloxy)anthra[9,1,2-cde-]benzo[rst]pentaphene-5-10-dione, octadecanoic acid, 5,10-dihydro-5,10-dioxoanthra [9,1,2-cde]benzo[rst]pentaphene-16,17-diylester, dihydroxydibenzanthrone, benzenesulfonic acid, 4,4',4",4"'-[[2, 9-bis[2,6-bis(1-methylethyl)phenyl]-1,2,3,8,9,10-hexahydro-1,3,8,10-tetraoxoanthra[2,1,9-def:6,5,10-d'e'f'] diisoquinoline-5,6,12,13-tetrayl]tetrakis(oxy)]tetrakis-, benzeneethanaminium, 4,4',4",4"'-[[2,9-bis[2,6-bis(1-methylethyl)phenyl]-1,2,3,8,9,10-hexahydro-1,3,8,10-tet-raoxoanthra[2,1,9-def:6,5,10-d'e'f']diisoquinoline-5,6,12, 13-tetrayl]tetrakis(oxy)]tetrakis[N,N,N-trimethyl-], and derivatives thereof.

(Average Particle Size of Dye Resin Particles)

The average particle size of the dye resin particles is preferably 30 to 300 nm, more preferably 40 nm to 200 nm, because this enables to suitably observe bright spots even under a general-purpose fluorescence microscope. When the average particle size is larger than 300 nm, the number of bright spots per cell that are observed after staining is reduced and this makes it difficult to observe bright spots, whereas when the average particle size is smaller than 30 nm, the number of bright spots per cell is increased and this also makes it difficult to observe bright spots.

(Chemical Modifier)

As a chemical modifier used for chemical modification of the surfaces of the dye resin particles, the below-described amino group-introducing reagents and PEGylation reagents can be used. Such chemical modifiers are capable of not only controlling the zeta potential of the fluorescent nanoparticles in water of pH 7.0 or that of the fluorescent nanoparticles in a buffer of pH 6.0 to 8.0, but also functioning to bind a biomolecule-recognizing molecule to the dye resin particles.

(Amino Group-Introducing Reagent)

As an amino group-introducing reagent, a variety of known reagents capable of appropriately introducing an amino group in accordance with the type of the dye resin particles can be used. Examples of the amino group-introducing reagent that can be preferably used include etha-nolamine, aminoalkyl group-containing triethoxysilanes (such as 3-aminopropyltriethoxysilane: APS), aminoalkyl group-containing secondary or tertiary amines (such as tris(2-aminoethyl)amine: TAEA) and alkanes substituted with two or more aminoalkoxy groups (such as 1,2-bis(2-aminoethoxy)ethane: BAEE, 1, 11-Diamino-3, 6, 9-tri-oxaundecan and 2,2'-oxybis(ethylamine)).

In the case of dye resin particles composed of a thermo-setting resin, a silanol group or an amino group of the amino group-introducing reagent undergoes dehydration or deal-coholization reaction with a hydroxyl group or ether of the dye resin particles, thereby an amino group is introduced. Meanwhile, in the case of dye resin particles composed of a thermoplastic resin, an amino group is introduced by reaction between an epoxy group of glycidyl methacrylate and ammonia or a polyfunctional amine or by reaction between a carboxyl group or a sulfone group and a polyfunctional amine.

(PEGylation Reagent)

As a PEGylation reagent, a variety of known reagents capable of appropriately adding a PEG chain in accordance with the type of the dye resin particles and/or the type of the amino group-introducing reagent can be used.

As for the length of PEG, a PEG having 4 to 24 oxyethylene units ($-CH_2CH_2-O-$) is preferred from the standpoint of easily controlling the zeta potential of the fluorescent nanoparticles in water of pH 7.0 to be in a range of $-10$ mV to $-60$ mV and the zeta potential of the fluorescent nanoparticles in a buffer of pH 6.0 to pH 8.0 to be 0 mV to $-10$ mV. When the number of the oxyethylene units ($-CH_2CH_2-O-$) is less than 4, it is difficult to reduce the zeta potential of the fluorescent nanoparticles, whereas when the number of the oxyethylene units ($-CH_2CH_2-O-$) is greater than 24, the zeta potential of the fluorescent nanoparticles in water of pH 7.0 or that of the fluorescent nanoparticles in a buffer of pH 6.0 to pH 8.0 may be reduced excessively.

Further, by binding the biomolecule-recognizing molecule to the dye resin particles through a PEG having the above-described appropriate length, as compared to a case where the biomolecule-recognizing molecule is (directly) bound to the dye resin particles without such a PEG, the binding of the fluorescent nanoparticles to the biomolecule to be stained is improved and the staining accuracy can thus be improved.

When binding a PEG chain to amino groups (that may be introduced by an amino group-introducing reagent) of the dye resin particles, a PEGylation reagent containing a suc-cinimide ester group of PEG is preferably used. In this case, the succinimide ester group reacts with the amino groups of the dye resin particles, thereby PEG is added to the dye resin particles.

When binding a PEG chain to sulfhydryl groups (SH groups) of the dye resin particles, a maleimide group-containing PEGylation reagent is preferably used. In this case, the maleimide group of PEG reacts with the SH groups of the dye resin particles, thereby PEG is added to the dye resin particles. Such SH groups correspond to amino groups of the dye resin particles that are converted into SH groups by S-mercaptoethylamine hydrochloride, N-succinimidyl-S-acetylthioglycolate (SATA) or 2-iminothiolane.

In cases where the below-described biomolecule-recognizing molecule is bound to the dye resin particles through PEG, it is desired to use, as a PEGylation reagent, a compound (PEG linker) which has a reactive group linkable with the dye resin particles and/or amino group-introducing reagent at a terminal of PEG and a reactive group (such as a maleimide group) linkable with the biomolecule-recognizing molecule at the other terminal. Examples of such a PEG linker include SM(PEG)n represented by the following Formula (n=2 to 24, manufactured by Thermo Fisher Scientific K.K.).

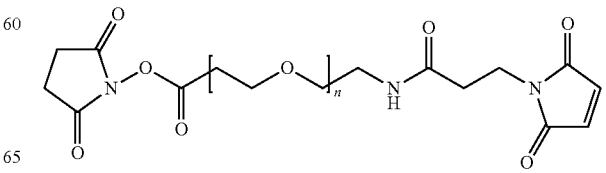

(Biomolecule-Recognizing Molecule)

The biomolecule-recognizing molecule, the other element constituting the fluorescent nanoparticles of the present invention, is a molecule specifically binding to a biomolecule to be stained and is used with being bound to the above-described dye resin particles. Examples of a combination of a "specific biomolecule" and a "biomolecule-recognizing molecule" specifically binding thereto include combinations of biotin-(strept)avidin, antigen-antibody and sugar chain-lectin. In accordance with such a combination, the phrase "specifically bind(ing)" can be interpreted as a general term used in the technical field to which the present invention belongs; however, it can also be defined by association constant ($K_A$) or an inverse number thereof, dissociation constant ($K_D$) (see Table 1 below).

That is, the biomolecule-recognizing molecule used in the present invention can be defined as a biomolecule having an association constant ($K_A$) for a biomolecule to be stained in a range of $1\times10^5$ to $1\times10^{12}$. When the association constant ($K_A$) is within this range, the biomolecule can be treated as a biomolecule-recognizing molecule "specifically binding" to the biomolecule to be stained, whereas when the association constant ($K_A$) is outside the range (less than $1\times10^5$), it cannot be said that the biomolecule "specifically binds" to the biomolecule to be stained, so that the biomolecule cannot be treated as a biomolecule-recognizing molecule in the present invention. Similarly, the biomolecule-recognizing molecule used in the present invention can also be defined as a biomolecule having a dissociation constant ($K_D$) for a biomolecule to be stained in a range of $1\times10^{-5}$ to $1\times10^{-12}$.

TABLE 1

| | Dissociation constant $K_D$ | Association constant $K_A$ |
|---|---|---|
| Definition | $\frac{(A)(B)}{(AB)} = \frac{Kd}{Ka}$ | $\frac{(AB)}{(A)(B)} = \frac{Ka}{Kd}$ |
| Unit | [M] | [M$^{-1}$] |
| Description | The higher the $K_D$, the lower the affinity. | The higher the $K_A$, the higher the affinity. |
| Standard range | $1\times10^{-5}$ to $1\times10^{-12}$ | $1\times10^5$ to $1\times10^{12}$ |

(cited from the homepage of GE Healthcare Japan)

Examples of binding between a biomolecule and a biomolecule-recognizing molecule that satisfies this condition include an intracellular antigen-antibody binding having an association constant ($K_A$) of $1\times10^9$ and a biotin-streptavidin binding having an association constant ($K_A$) of $1\times10^{12}$; however, in addition thereto, a combination of a biomolecule and a biomolecule-recognizing molecule that bind with an association constant ($K_A$) comparable to the above can also be selected. Here, an antibody against a certain antigen that can be prepared by a conventional method (immunization), preferably a commercially available antibody, usually has an association constant ($K_A$) in the above-described range; therefore, in an embodiment where the antigen is the biomolecule to be stained, such an antibody can be utilized as a biomolecule-recognizing molecule. The association constant ($K_A$) can be measured by a known method.

Such a biomolecule-recognizing molecule having a high association constant ($K_A$) as described above is bound to the dye resin particles through a PEG chain as required, and the biomolecule-recognizing molecule can thereby be bound to a biomolecule to be stained with a binding strength greater than the repulsive force generated by the zeta potential of the fluorescent nanoparticles in a specific negative range.

In cases where an antibody is used as the biomolecule-recognizing molecule, a variety of antibodies including those which constitute an antibody pharmaceutical can be used. In the present invention, the term "antibody" is used with a meaning that includes arbitrary antibody fragments or derivatives, encompassing a variety of antibodies such as Fabs, Fab'2s, CDRs, humanized antibodies, polyfunctional antibodies and single-chain antibodies (ScFv).

Representative examples of the biomolecule-recognizing molecule include antibodies against growth regulator receptors and metastasis regulator receptors of cancer cells that relate to drug selection for various cancers. For example, HER2 (human epidermal growth factor receptor type 2) existing on the cell surfaces is a protein that is important as an immunostaining target in the drug selection for breast cancer. The anti-HER2 antibody specifically binding thereto is suitable as the biomolecule-recognizing molecule to be bound to the dye resin particles. Examples of the biomolecule-recognizing molecule also include anti-actin antibodies that specifically bind to actin forming the cytoskeleton. In addition, it is also possible to use such a biomolecule-recognizing molecule having a high binding strength as described above against a specific biomolecule.

In other words, as long as such a biomolecule-recognizing molecule having a high binding strength as described above is present, a variety of biomolecules can be the staining target. Examples thereof include various biomolecules that serve as antigens with which antibodies, representative examples of the biomolecule-recognizing molecule, can be prepared. The "antigen" is generally a protein (such as a polypeptide or oligopeptide) or an amino acid (including a modified amino acid); however, for example, nucleic acids (such as DNAs, RNAs, polynucleotides, oligonucleotides and PNAs (peptide nucleic acids), which may be single-stranded or double-stranded; nucleosides; nucleotides; and modified molecules thereof), saccharides (such as oligosaccharides, polysaccharides and sugar chains) and lipids as well as modified molecules and complexes thereof can also be the antigen.

In addition to the above-described antigens such as HER2 that relate to cancer, inflammatory cytokines, such as TNF-α (Tumor Necrosis Factor α) and IL-6 (Interleukin-6) receptor, and virus-associated molecules such as RSV F protein can also be the biomolecule to be stained. A combination of a biomolecule to be stained and a biomolecule-recognizing molecule specifically binding thereto can be selected in accordance with the intended purpose.

It is noted here however that, in the present invention, the "biomolecule to be stained" is not restricted to the very protein to be detected such as the above-described receptor relating to the drug selection for cancer, and a biomolecule capable of indirectly binding the fluorescent nanoparticles to the protein to be detected can also be treated as a biomolecule to be stained". For example, in such an embodiment of immunostaining where an antibody (primary antibody) recognizing a protein to be detected as an antigen is bound to the protein, this primary antibody corresponds to the "biomolecule to be stained" and the fluorescent nanoparticles can contain, as a biomolecule-recognizing molecule, an antibody (secondary antibody) that recognizes this primary antibody as an antigen. Alternatively, in such an embodiment of immunostaining where an antibody (primary antibody) recognizing a protein to be detected as an antigen is bound to the protein first as described above and then a complex of biotin and an antibody (secondary antibody) recognizing this primary antibody as an antigen is further bound, this biotin corresponds to the "biomolecule to be stained" and the fluorescent nanoparticles can contain streptavidin specifically binding to this biotin as a biomolecule-recognizing molecule.

(Binding of Biomolecule-recognizing Molecule to Dye Resin Particles)

The mode of binding a biomolecule-recognizing molecule to the dye resin particles is not particularly restricted; however, it is more preferred to indirectly bind the biomolecule-recognizing molecule to the dye resin particles through the above-described PEG linker than to directly binding the biomolecule-recognizing molecule to the dye resin particles. The biomolecule-recognizing molecule can be bound through a covalent bond, an ionic bond, a hydrogen bond, a coordinate bond, physical adsorption, chemical adsorption or the like; however, from the standpoint of the binding stability, a bond having a high binding strength, such as a covalent bond, is preferred.

When binding the biomolecule-recognizing molecule and the dye resin particles through PEG, for example, they can be bound via a covalent bond by allowing a maleimide group of a PEG linker added to the dye resin particles to react with a thiol group of the biomolecule-recognizing molecule.

Upon binding the biomolecule-recognizing molecule to the dye resin particles, it is desired to covert the reactive group(s) on the dye resin particle side into other reactive group(s), while not converting the intrinsic reactive group(s) of the biomolecule-recognizing molecule into other reactive group(s) as much as possible. This is because, for example, when the biomolecule-recognizing molecule is a protein such as an antibody, conversion of a reactive group of the antibody such as SH group may change the stereostructure of the molecule and this potentially impairs the intrinsic binding capacity of the biomolecule-recognizing molecule.

For example, a reactive group of the dye resin particles is converted into an amino group using an amino group-introducing reagent as described above and, after adding a PEG linker to this amino group, a reaction where an SH group of the biomolecule-recognizing molecule is bound to a free maleimide group of the PEG linker is performed, thereby the biomolecule-recognizing molecule is bound to the dye resin particles.

In cases where the biomolecule-recognizing molecule is a protein, since SH groups are usually in the form of disulfide groups (S—S) and some of the groups existing as SH groups greatly affect the protein functions by, for example, assuming a structure bound with a metal ion and serving as reaction center, such SH groups cannot be used for the above-described binding. In order to use an SH group of the biomolecule-recognizing molecule for the above-described binding, it is required to (1) reduce a disulfide structure (S—S) into SH groups to be used for the binding, or (2) introduce an SH group to be used for the binding.

For the reduction of disulfide, mercaptoethylamine hydrochloride (MEA), β-mercaptoethanol (β-ME), dithiothreitol or the like is used. Reduction of all of disulfides in a protein into thiol groups (—SH) may cause the protein to lose its functions; therefore, it is required to adjust the concentration of a reducing agent such that only some of the disulfides are reduced into SH groups to be used. Meanwhile, examples of an SH group-introducing reagent include N-succinimidyl-S-acetylthioacetate (SATA) and 2-iminothiolane, and the reduction into SH groups and the SH group introduction themselves can be performed by a known method.

<Method of Producing Fluorescent Nanoparticles>

The fluorescent nanoparticles according to the present invention can be produced by a production method comprising the step of chemically modifying the surfaces of dye resin particles having a fluorescent dye embedded therein or immobilized thereon so as to impart the dye resin particles with a zeta potential that allows the resulting fluorescent nanoparticles as a whole to have a zeta potential of −10 mV to −60 mV in water of pH 7.0 or 0 mV to −10 mV in a buffer of pH 6.0 to 8.0. This step preferably includes chemical modification where an amino group is imparted to the dye resin particles by binding thereto an amino group-containing compound and then PEG and a biomolecule-recognizing molecule are bound to the amino group. Specifically, such a method of producing the fluorescent nanoparticles may take an embodiment which comprises, for example, the following steps: (1) mixing step; (2) polymerization step; (3) washing step; and (4) addition step. Among these steps, the (4) addition step is the step that relates to the above-described chemical modification.

(1) Preparation of Starting Material and Mixing Step

The mixing step is a step of mixing the above-described fluorescent dye with one or more monomers or oligomers used for the formation of dye resin particles. In the materials to be mixed, a proton donor and a polymerization reaction accelerator can also be optionally included.

By mixing the fluorescent dye and the resin monomer(s) in advance, the fluorescent dye and the one or more monomers or oligomers are bound with each other, so that the fluorescent dye can be easily incorporated into the resulting dye resin particles. For this binding, the fluorescent dye and the resin monomer(s) may be ionically bound with each other via a substituent or chemical moiety having an opposite electric charge, or they may be covalently bound via a substituent or chemical moiety.

Specific examples of the ionic bonding include a case where a resin which is a melamine and a fluorescent dye which is sulforhodamine are bound via an ionic bond formed by a positively charged nitrogen atom (such as —NH$^+$—) in the resin and a sulfo group (SO$_3^-$) of the fluorescent dye. Further, specific examples of the covalent bonding include a case where 4-aminostyrene and Sulforhodamine 101 acid chloride are allowed to react with each other to form a covalent bond (—NH$_2$—SO$_2$—) (the resulting reaction product is used as a comonomer of styrene-based nanoparticles).

The above-described bonding method is not particularly restricted and, in addition to a method in which a monomer used as a resin material is polymerized after binding a fluorescent dye thereto, a method of binding a fluorescent dye to a polymer as well as any other methods appropriate for the intended purpose can be employed.

(Proton Donor)

In cases where a resin monomer and a fluorescent dye are ionically bound, a proton donor which actively supplies H$^+$ and imparts a positive charge to a substituent (such as NH$_2$) of the resin monomer (such as melamine) and/or a substituent of the fluorescent dye can be used as well. Examples of such a proton donor include formic acid, acetic acid, p-toluenesulfonic acid and their equivalents.

When a substituent attached to the fluorescent dye is an acid such as carboxylic acid or sulfonic acid, the acid is also capable of functioning as a proton donor because a proton dissociated therefrom is added to the substituent (such as NH$_2$) of the fluorescent dye and imparts thereto a positive charge. Conversely, it is also possible to use a proton acceptor which actively removes H$^+$ and imparts a negative charge to a substituent of the resin monomer and that of the fluorescent dye. For example, a base such as sodium hydroxide functions as a proton acceptor.

(Polymerization Reaction Accelerator)

As a reaction accelerator of a thermoplastic resin, for example, a known polymerization catalyst such as a metal can be used. Meanwhile, as a reaction accelerator of a thermosetting resin, for example, an acid can be used. Melamine resins, urea resins, xylene resins and phenol resins are all known to be facilitated to react by an acid catalyst. As the acid, for example, formic acid, acetic acid, sulfuric acid, hydrochloric acid, nitric acid, p-toluenesulfonic acid and dodecylbenzenesulfonic acid are known. The reaction of a thermosetting resin can be advanced only by heating; however, since an addition of a reaction accelerator allows the reaction to proceed at a lower temperature, a reaction accelerator can be added in such a range where the reaction and performance thereof can be controlled.

(2) Polymerization Step

The polymerization step is a step of forming dye resin particles by heat-curing or radical polymerization of the resin monomer(s) or oligomers(s) electrically or covalently bound with the fluorescent dye or by radical polymerization of the resin monomer(s) or oligomer(s) while incorporating the fluorescent dye. The reaction conditions of the polymerization step (temperature and time) are determined based on the composition(s) of the monomer(s) or oligomer(s) to be polymerized, and the polymerization can be performed in accordance with a known method.

For example, polystyrene-based nanoparticles in which a fluorescent organic dye is embedded can be produced by the copolymerization method described in U.S. Pat. No. 4,326,008 (1982) where an organic dye having a polymerizable functional group is used, or by the method described in U.S. Pat. No. 5,326,692 (1992) where a fluorescent organic dye is impregnated into polystyrene nanoparticles.

(3) Washing Step

The washing step is a step of removing impurities, such as excess resin material, fluorescent dye and emulsifying agent, from the thus obtained dispersion of the dye resin particles. Washing is performed, for example, as follows: after recovering resin components from the reaction solution by centrifugation and removing the resulting supernatant, ultrapure water is added to the recovered resin components and the resultant is ultrasonicated for re-dispersion of the resin components. It is preferred that a series of these washing operations—centrifugation, supernatant removal and re-dispersion into ultrapure water—be repeated a plurality of times until the resulting supernatant no longer shows any absorption or fluorescence emission attributed to the resin or the dye.

(4) Addition Step

The addition step is a step of subjecting the surfaces of the dye resin particles obtained from the washing step (3) to an appropriate chemical modification, thereby adjusting the zeta potential of the fluorescent nanoparticles in water of pH 7.0 to be −10 my to −60 my or that of the fluorescent nanoparticles in a buffer of pH 6.0 to 8.0 to be 0 mV to −10 mV. This step is performed, for example, as follows: after imparting amino groups to the dye resin particles by binding the above-described amino group-containing compound such as SATA or TAEA to the dye resin particles, PEG is allowed to bind to the amino groups and the biomolecule-recognizing molecule is further bound to this PEG.

(Introduction of Amino Group)

Using the above-described amino group-introducing reagent, amino groups can be introduced to the dye resin particles by a known means.

Specifically, the dye resin particles obtained in the polymerization step are dispersed in water and the amino group-introducing reagent is allowed to react with the resulting dispersion. After the completion of the reaction, fluorescent nanoparticles having amino groups introduced to their surfaces can be obtained by centrifugation or filtration.

The type and the amount of the amino group-introducing reagent to be used as well as the conditions such as reaction temperature and reaction time can each be adjusted in an appropriate range taking into consideration the properties of the dye resin particles and the like, such that fluorescent nanoparticles whose zeta potential in water of pH 7.0 or in a buffer of pH 6.0 to 8.0 satisfies the prescribed condition can be eventually obtained.

(Addition of PEG)

Using the above-described PEGylation reagent, PEG can be introduced to the dye resin particles by a known means. For example, PEG is added by allowing an N-hydroxysuccinimidyl ester group of the PEGylation reagent to react with the amino groups introduced to the dye resin particles. Specifically, PEG can be introduced by adjusting a PEGylation reagent, succinimidyl-[(N-maleimidopropionamido)-dodecaethyleneglycol]ester ("SM(PEG)$_{12}$" (trademark), manufactured by Thermo Fisher Scientific K.K.), with PBS containing 2 mM (molar concentration) of EDTA to a final concentration of 10 mM and then allowing the resulting solution to react with the particles adjusted to a concentration of 3 nM at room temperature for 30 minutes.

The type and the amount of the PEGylation reagent to be used as well as the conditions such as reaction temperature and reaction time can each be adjusted in an appropriate range taking into consideration, for example, the properties of the dye resin particles and/or the amino group-introducing reagent as well as the properties of the biomolecule-recognizing molecule, such that fluorescent nanoparticles whose zeta potential in water of pH 7.0 or in a buffer of pH 6.0 to 8.0 satisfies the prescribed condition can be eventually obtained.

(Addition of Biomolecule-Recognizing Molecule)

For example, an antibody can be bound to the fluorescent nanoparticles by, in accordance with a known method, allowing the maleimide group of PEG added to the dye resin particles to react with the thiol group added to the biomolecule-recognizing molecule, or allowing the amino group introduced to the dye resin particles or the amino group intrinsically included in the fluorescent dye and resin monomer units contained in the dye resin particles to react with the carboxyl group of the biomolecule-recognizing molecule. Specifically, streptavidin is subjected to a thiol group addition treatment using 2-iminothiolane or SATA and excess reaction reagent is then removed through a gel filtration column to obtain a solution of streptavidin capable of binding to silica particles.

The PEG-added dye resin particles obtained above and this streptavidin are mixed in PBS containing 2 mM of EDTA and allowed to react for 1 hour, thereby the dye resin particles and streptavidin can be bound with each other.

The type and the amount of the biomolecule-recognizing molecule to be used as well as the conditions such as reaction temperature and reaction time can each be adjusted in an appropriate range taking into consideration, for example, the properties of the dye resin particles and/or the amino group-introducing reagent and the use of the resulting fluorescent nanoparticles, such that fluorescent nanoparticles whose zeta potential in water of pH 7.0 or in a buffer of pH 6.0 to 8.0 satisfies the prescribed condition and which are capable of sufficiently binding to the biomolecule to be stained can be obtained.

In cases where the zeta potential of the fluorescent nanoparticles in a buffer of pH 6.0 to pH 8.0 is controlled externally, the zeta potential may be comprehensively controlled to be in a range of 0 mV to −10 mV by adjusting the pH of the buffer or by arbitrarily incorporating one or more other compounds capable of controlling the zeta potential, such a protein, a surfactant and/or a preservative, in a prescribed amount.

As the protein, any protein capable of controlling the zeta potential can be used with no particular restriction, and examples thereof include proteins and caseins that are generally known as blocking agents of BSA and the like. It is desired that such a protein be incorporated in an amount of 10% by weight or less (for example, in a range of 1 to 10% by weight) with respect to the whole buffer.

As the surfactant, any surfactant capable of controlling the zeta potential can be used with no particular restriction, and examples thereof include Tween 20 (registered trademark). It is desired that the surfactant be incorporated in an amount of 0.1% by weight or less with respect to the whole buffer.

As the preservative, any preservative capable of controlling the zeta potential can be used with no particular restriction, and examples thereof include sodium azide ($NaN_3$). It is desired that the preservative be incorporated at a concentration of 0.015 N in the buffer.

[Method of Staining and Observing Biomolecule]

A method of staining and observing a biomolecule will now be described.

The biomolecule staining method is a method of staining and observing a biomolecule using the above-described fluorescent nanoparticles and specifically comprises: (a) the step of staining cells with the fluorescent nanoparticles; (b) the step of taking an image of fluorescence emitted from the fluorescent dye of the stained cells in a single viewing field; and (c) the step of recognizing only those pixels detected in the image obtained in the step (b) as effective bright spots.

1. Regarding the Step (a)

The step (a) is a step of allowing the fluorescent nanoparticles containing a biomolecule-recognizing molecule to react with biomolecules of cells and thereby staining a biomolecule to be stained through a specific bond (such as antigen-antibody reaction or streptavidin-biotin bond) between the biomolecule-recognizing molecule of the fluorescent nanoparticles and the biomolecule. The staining method and the preparation of a tissue section are not particularly restricted and can be performed by a known method.

For example, in cases where a paraffin-embedded section widely used as a pathological section is used as a section of tissue cells, the step (a) can be performed by the following procedure.

(1) Deparaffinization Step

A section of histopathological cells is immersed in xylene contained in a vessel to remove paraffin. The temperature of this process is not particularly restricted and, for example, it can be performed at room temperature. The immersion time is preferably 3 minutes or longer but not longer than 30 minutes. As required, xylene may be replaced anew in the middle of the immersion.

Then, the section is immersed in ethanol contained in a vessel to remove xylene. The temperature of this process is not particularly restricted and it can be performed at room temperature. The immersion time is preferably 3 minutes or longer but not longer than 30 minutes. As required, ethanol may be replaced anew in the middle of the immersion.

The section is further immersed in water contained in a vessel to remove ethanol. The temperature of this process is not particularly restricted and it can be performed at room temperature. The immersion time is preferably 3 minutes or longer but not longer than 30 minutes. As required, water may be replaced anew in the middle of the immersion.

(2) Activation Step

In accordance with a known method, activation of the biomolecule to be stained is performed. The activation conditions are not particularly defined; however, as an activation solution, for example, a 0.01 M citrate buffer (pH 6.0), a 1 mM EDTA solution (pH 8.0), 5% urea or a 0.1 M Tris-HCl buffer can be used. As a heating apparatus, for example, an autoclave, a microwave oven, a pressure cooker or a water bath can be used. The activation can be performed at a temperature of 50 to 130° C. for a duration of 5 to 30 minutes.

Then, the thus activated section is immersed and washed in PBS contained in a vessel. The temperature of this process is not particularly restricted and it can be performed at room temperature. The immersion time is preferably 3 minutes or longer but not longer than 30 minutes. As required, PBS may be replaced anew in the middle of the immersion.

(3) Staining with Fluorescent Nanoparticles

A PBS dispersion (staining solution) of the fluorescent nanoparticles prepared in the above-described manner is placed on the pathological section and allowed to react with the biomolecule to be stained. The temperature of this process is not particularly restricted and it can be performed at room temperature. The reaction time is preferably 30 minutes or longer but not longer than 24 hours.

The concentration of the fluorescent nanoparticles in the dispersion can be set at usually 1 to 0.005 nM, preferably 0.5 to 0.02 nM. Even when the fluorescent nanoparticles of the present invention are used at a relatively high concentration, non-specific binding thereof to cell nuclei or other parts of the tissue and agglutination of the fluorescent nanoparticles can be suppressed.

Then, the thus stained section is immersed in PBS contained in a vessel to remove unreacted fluorescent nanoparticles. The temperature of this process is not particularly restricted and it can be performed at room temperature. The immersion time is preferably 3 minutes or longer but not longer than 30 minutes. As required, PBS may be replaced anew in the middle of the immersion. Here, for morphological observation of the tissue, the section may also be subjected to hematoxylin-eosin staining. Thereafter, a cover glass is placed on the section for mounting. As required, a commercially available mounting medium may be used as well.

2. Regarding the Step (b)

The step (b) is a step of taking an image of fluorescence emitted from the fluorescent dye of the cells stained in the step (a) in a single viewing field. The image can be obtained in the form of an image containing three-dimensional information using a confocal fluorescence microscope. For the imaging, an excitation light source and an optical filter for fluorescence detection that conform to the maximum absorption wavelength and the fluorescence wavelength of the fluorescent substance in use are selected.

3. Regarding the Step (c)

The step (c) is a step of recognizing only those pixels detected in the image obtained in the step (b) as effective bright spots. Specifically, this step comprises: (i) measuring the number of pixels and the emission brightness in the image obtained in the step (b); and (ii) obtaining bright spot data by counting, as bright spots, only those pixels in the image that have not less than an emission brightness regarded as light being emitted and arithmetically processing the measurement result. Based on the number of bright spots or the emission brightness, the expression level of the biomolecule to be stained can be determined. The measurement of the number of bright spots or the emission brightness can be performed using a commercially available image analysis software, such as an automatic total bright spot measuring software "G-Count" manufactured by G-Angstrom K.K.

The actions and effects of the fluorescent nanoparticles of the present invention will now be described.

(1) When cells (intracellular pH is neutral) are stained with the fluorescent nanoparticles having a zeta potential of −10 mV to −60 mV at pH 7.0 or 0 mV to −10 mV in a buffer of pH 6.0 to 8.0, biomolecules and the fluorescent nanoparticles electrically repel each other and this makes nonspecific binding between the fluorescent nanoparticles and the biomolecules unlikely to occur. Further, since the fluorescent nanoparticles comprises a biomolecule-recognizing molecule specifically binding to a biomolecule to be stained, the fluorescent nanoparticles are capable of binding with the biomolecule to be stained through interaction far stronger than the above-described electrical repulsive force.

(2) As long as the surfaces of the fluorescent dye-containing dye resin particles are chemically modified with a compound capable of controlling the zeta potential, for example, by utilizing a compound for binding the biomolecule-recognizing molecule with the dye resin particles, the zeta potential of the fluorescent nanoparticles in water of pH 7.0 or that in a buffer of pH 6.0 to 8.0 can be controlled in the above-described range.

(3) As long as the above-described chemical modification is performed by introducing an amino group to the dye resin particles, binding PEG to the amino group and then binding the biomolecule-recognizing molecule to this PEG, the zeta potential of the fluorescent nanoparticles in water of pH 7.0 or that in a buffer of pH 6.0 to 8.0 can be easily controlled based on the combination of the type of the above-described compound and the type (chain length) of the PEG.

(4) As long as the above-described amino group-containing compound is in a state of being bound with the dye resin particles and has one free amino group, a scaffold for PEG addition can be added thereto. Further, when the amino group-containing compound has two or more free amino groups, scaffolds for PEG addition can be further added, so that the number of bright spots per cell can be increased. Moreover, since PEG can be added in a branched chain form, the zeta potential of the fluorescent nanoparticles in water of pH 7.0 or that in a buffer of pH 6.0 to 8.0 can be easily controlled.

(5) As long as the PEG has 4 to 24 oxyethylene units (—$CH_2CH_2$—O—), the zeta potential of the fluorescent nanoparticles in water of pH 7.0 can be easily controlled in a range of −10 mV to −60 mV or the zeta potential in a buffer of pH 6.0 to 8.0 can be easily controlled in a range of 0 mV to −10 mV.

(6) When the amino group-containing compound is 1,2-bis(2-aminoethoxy)ethane (BAEE), since BAEE has oxyethylene units (—$CH_2CH_2$—O—), it can contribute to zeta potential control in the same manner as PEG. Further, when the amino group-containing compound is tris(2-aminoethyl) amine (TAEA), since TAEA has an amino group at each of the three branched terminals and is thus added to the dye resin particles through one of these amino groups, the number of the scaffolds for PEG addition can be doubled and the number of bright spots per cell can thereby be increased.

(7) As long as the dye resin particles are composed of a thermosetting resin, particularly a melamine resin, when the dye resin particles are formed by polymerization using monomers of the thermosetting resin and the fluorescent dye, the fluorescent dye is trapped in the network structure of the resulting thermosetting resin; therefore, even in a system where an organic solvent is used, elution of the fluorescent dye does not occur and this enables to perform dehydration, clearing and mounting of a tissue section to be stained.

(8) In the fluorescent nanoparticles in which streptavidin obtained through a reaction with N-succinimidyl-S-acetyl-thioacetate (SATA) or 2-iminothiolane is bound to the dye resin particles as the biomolecule-recognizing molecule, since this biomolecule-recognizing molecule is modified with an amino group and/or an SH group, the zeta potential of the fluorescent nanoparticles can be controlled by this modification as well.

(9) When the above-described buffer further contains at least either a protein or a surfactant, the zeta potential of the fluorescent nanoparticles can be easily controlled by changing the amount and the type of the protein or the surfactant.

(10) When the above-described staining is immunostaining, since biomolecules and the fluorescent nanoparticles are bound together with a binding strength much stronger than antigen-antibody reaction, the biomolecules and the fluorescent nanoparticles are allowed to exhibit electrical repulsion attributed to their zeta potentials in a wide range of strength lower than the binding strength. Consequently, in the production of the fluorescent nanoparticles, even if the resulting particles have varying zeta potentials, specific binding between the fluorescent nanoparticles and the biomolecule to be stained is established more reliably, so that immunostaining can be performed with high accuracy.

(11) When the average particle size of the fluorescent nanoparticles is larger than 300 nm, the number of bright spots per cell that are observed after staining is reduced and this makes it difficult to observe bright spots, whereas when the average particle size of the fluorescent nanoparticles is smaller than 30 nm, the number of bright spots per cell is increased and this also makes it difficult to observe bright spots. Therefore, as long as the average particle size of the fluorescent nanoparticles is 30 to 300 nm, bright spots can be suitably observed even under a general-purpose fluorescence microscope. Further, if the average particle size of the fluorescent nanoparticles is 40 to 200 nm, bright spots can be more suitably observed.

EXAMPLES

Examples and Comparative Examples according to the present invention will now be described referring to the drawings.

For the fluorescent nanoparticles of Examples and Comparative Examples, the items shown in Table 2 below were measured or evaluated by the following methods.

(Measurement of Zeta Potential) As for the zeta potential of fluorescent nanoparticles in water of pH 7.0, an aqueous dispersion (pH 7.0) containing the subject fluorescent nanoparticles at a concentration of 2 mg/mL was prepared and the zeta potential of the aqueous dispersion was measured using a zeta potential-measuring device ("Zetasizer Nano", manufactured by Malvern Instruments Ltd.).

As for the zeta potential of fluorescent nanoparticles in buffers of pH 6.0 to 8.0, buffers (PBS, Tris-HCl and phosphate buffer (excluding PBS)) of pH 6.0 to pH 8.0 containing the subject fluorescent nanoparticles at a concentration of 2 mg/mL were each prepared and the zeta potentials of the fluorescent nanoparticles were measured using a zeta potential-measuring device ("Zetasizer Nano", manufactured by Malvern Instruments Ltd.).
(Method of Evaluating Reagent Dispersibility in Fluorescent Nanoparticles)

A solution in which the subject fluorescent nanoparticles produced were dispersed in a 1% BSA-containing PBS (phosphate-buffered physiological saline) at a final concentration of 0.1 nM was prepared in an amount of 1.5 mL, and light emitted from this solution at 580-nm excitation was measured using a fluorophotometer ("F-7000", manufactured by Hitachi, Ltd.). Further, after leaving the solution to stand at 4° C. for 1 day, the absorbance was measured in the same manner as described above. From the measurement results, the retention rate of reagent dispersion in the fluorescent nanoparticles was calculated using the following equation, and an evaluation "○" was given to the fluorescent nanoparticles having a retention rate of reagent dispersion of 95% or higher while an evaluation "x" was given to the fluorescent nanoparticles having a retention rate of reagent dispersion of lower than 95% (see Table 1).

Retention rate of reagent dispersion=absorbance after 1 day incubation/absorbance immediately after dispersion (×100%)

(Method of Evaluating Non-Specific Adsorption of Fluorescent Nanoparticles to Cell Nuclei)

Tissue array slides, on which an antigen-antibody reaction using a biotin-added antibody had not been carried out on a cell antigen (biomolecule to be stained), were each stained with a dispersion (0.2 nM or 0.005 nM) of fluorescent nanoparticles having streptavidin and subsequently observed to measure the number of bright spots existing in cell nucleus for arbitrarily selected 60 cells by an ImageJ Find Maxima method. The average number of bright spots per cell nucleus (=number of bright spots in observed cell nuclei/number of observed cell nuclei) was calculated and evaluated based on whether or not the value was 1 or larger. In Table 2, the calculated values are shown under the evaluation item "Adsorption to cell nuclei", with values of 1 or larger being indicated as "x" and values of smaller than 1 being indicated as "○".
(Method of Evaluating Non-specific Binding of Fluorescent Nanoparticles to Whole Tissue)

A tissue array slide, on which an antigen-antibody reaction using a biotin-added antibody had not carried out on a cell antigen (biomolecule to be stained), was stained with a dispersion (0.2 nM) of fluorescent nanoparticles having streptavidin and subsequently observed to measure the number of bright spots existing over the whole cell for arbitrarily selected 60 cells by an ImageJ Find Maxima method. The average number of bright spots per cell (=number of bright spots in observed cells/number of observed cells) was calculated and evaluated based on whether or not the value was 1 or larger. In Table 2, the calculated values are shown under the evaluation item "Adsorption to whole tissue", with values of 1 or larger being indicated as "x" and values of smaller than 1 being indicated as "o".
(Method of Evaluating Elution of Dye from Fluorescent Nanoparticles)

an antigen-antibody reaction using a biotin-added antibody was carried out on a cell antigen (biomolecule to be stained) of a tissue array slide, and the tissue array slide was subsequently subjected to staining (immunostaining) with a dispersion (0.2 nM) of fluorescent nanoparticles conjugated with streptavidin. Then, the thus stained slide was observed to evaluate the presence or absence of bleeding of fluorescent dye. In Table 2, "○" indicates that bleeding of the fluorescent dye was not observed and "x" indicates that no bright spot could be confirmed due to bleeding of the fluorescent dye.
(Number of Bright Spots Per Cell (Average Number of Cell Bright Spots)

An antigen-antibody reaction using a biotin-added antibody was carried out on a cell antigen (biomolecule to be stained) of a tissue array slide, and the tissue array slide was subsequently subjected to staining (immunostaining) with a dispersion (0.2 nM) of fluorescent nanoparticles conjugated with streptavidin. Then, the thus stained slide was observed to examine the number of bright spots for 60 cells, and the average number of bright spots per cell was calculated (average number of cell bright spots).
(Method of Measuring Average Particle Size of Fluorescent Nanoparticles)

A photograph of the subject fluorescent nanoparticles was taken under a scanning electron microscope (SEM), the cross-sectional area was measured for a sufficient number of particles, and the particle size was determined as the diameter of a circular area corresponding to the respective measured values. In the present application, the arithmetic mean of the particle sizes of 1,000 particles was defined as the average particle size.

Example 1

A case where melamine-based particles according to the present invention were produced (prepared) will now be described. The term "melamine-based particles" means resin particles mainly containing melamine.
(1) Preparation of Starting Material and Mixing Step To 22.5 mL of pure water, 2.5 mg of a fluorescent dye "Sulforhodamine 101" (Texas Red dye, manufactured by Sigma-Aldrich) was dissolved. This solution was stirred for 20 minutes while keeping it at 70° C. using a hot stirrer. Then, 1.5 g of a water-soluble melamine resin "Nikalac MX-035" (manufactured by Nippon Carbide Industries Co., Ltd.) was added to the solution, and the resulting solution further stirred with heating for 5 minutes under the same condition.
(2) Polymerization Step To this heat-stirred solution, 100 μL of formic acid was added, and the solution was further stirred with heating for 20 minutes while maintaining the solution temperature at 60° C. Then, the solution was left to stand and allowed to cool to room temperature.
(3) Washing Step The thus cooled solution was transferred to a centrifugal tube and centrifuged for 20 minutes using a centrifugal machine at 12,000 rpm. The resulting supernatant of the centrifuged solution was removed to recover only the precipitates. The thus recovered precipitates were washed with ethanol by rinsing and then with water in the same manner.
(4) Addition Step As shown below, the surfaces of the melamine-based particles were chemically modified to adjust the zeta potential.

First, 1 mL of the melamine-based particles (dye resin particles) adjusted to a concentration of 1 nM after the above-described washing was mixed with 20 μL of ethanolamine and the resulting mixture was allowed to react at 70° C. for 1 hour. That is, an amino group was introduced to the melamine-based particles. The thus obtained melamine-based particles were adjusted with PBS (phosphate-buffered physiological saline) containing 2 mM of EDTA (ethylenediamine tetraacetic acid) to a concentration of 3 nM.

This solution of the melamine-based particles was mixed with SM(PEG)$_4$ (manufactured by Thermo Fisher Scientific K.K.; succinimidyl-[(N-maleimidopropionamido)-tetraethylene glycol]ester) to a final concentration of 10 mM, and the resulting mixture was allowed to react at room temperature for 1 hour. That is, the amino group introduced to the melamine-based particles as described above was allowed to react with the succinimide ester group at a terminal of SM(PEG)$_4$, thereby binding SM(PEG)$_4$ to the melamine-based particles.

This reaction solution was centrifuged at 10,000 G for 20 minutes and the resulting supernatant was removed to recover only the precipitates. Then, PBS containing 2 mM of EDTA was added to disperse the precipitates. The resulting dispersion was again centrifuged at 10,000 G for 20 minutes and the supernatant was removed to recover only the precipitates. Washing of the melamine-based particles by the series of operations from the precipitate-dispersing process and centrifugation was performed three more times. As a result, melamine-based particles in which the maleimide group at the other terminal of the above-described SM(PEG)$_4$ exists on the particle surfaces and the Texas Red dye is embedded were obtained. Further, when the average particle size of the thus obtained melamine-based particles was measured under an electron microscope by the above-described method, the average particle size was determined to be 150 nm.

On another front, streptavidin capable of binding to the melamine-based particles was prepared as follows.

First, 70 μL of 2-iminothiolane (manufactured by Pierce) adjusted to a concentration of 64 mg/mL was allowed to react with 40 μL of streptavidin (manufactured by Wako Pure Chemical Industries, Ltd.) adjusted to a concentration of 1 mg/mL at room temperature for 1 hour. That is, a protected thiol group (—NH—CO—CH$_2$—S—CO—CH$_3$) was introduced to the amino group of streptavidin.

Then, by a known hydroxylamine treatment, a free thiol group (—SH) was generated from the protected thiol group to perform a process of adding a thiol group (—SH) to streptavidin.

The resulting streptavidin solution was desalted through a gel filtration column (Zeba Spin Desalting Columns: manufactured by Funakoshi Co., Ltd.) to obtain streptavidin capable of binding to the melamine-based particles.

The whole amount of this streptavidin and 1 mL of the melamine-based particles adjusted with PBS containing 2 mM of EDTA to a concentration of 1 nM were mixed and allowed to undergo reaction where these molecules were bound at room temperature for 1 hour. The resultant was then centrifuged and washed with PBS containing 2 mM of EDTA, and only streptavidin-bound melamine-based particles (fluorescent nanoparticles) were recovered.

The zeta potential of the thus recovered fluorescent nanoparticles in water of pH 7.0 was measured to be −14 mV.
(Confirmation of Non-Specific Binding)

The thus obtained melamine-based particles were dispersed in PBS buffer (pH 7.4) at a concentration of 0.2 nM or 0.005 nM and the resulting dispersion was applied to a tissue array slide, which was subsequently left to stand at room temperature for 2 hours and washed with PBS buffer. Then, the tissue array slide which had been subjected to neither immunostaining nor morphological staining was irradiated with an excitation light of Sulforhodamine 101 to allow the fluorescent dye to emit fluorescence. The tissue array slide in this state was observed and photographed under a fluorescence microscope (BX-53, manufactured by Olympus Corporation) to confirm that hardly any fluorescence attributed to non-specific adsorption of the melamine-based particles to the biomolecule was observed. Further, bright spots were measured by an ImageJ Find Maxima method (see Table 2—Example 1 "Adsorption to cell nuclei" and "Adsorption to whole tissue" as well as FIG. 1(B)).
(Immunostaining)

Using the melamine-based particles, a human breast tissue was subjected to immunostaining and morphological staining as follows. As a tissue section to be stained, a tissue array slide (CB-A712 series, manufactured by Cosmo Bio Co., Ltd.) was used. This tissue array slide was deparaffinized and then washed for substitution with water. The washed tissue array slide was subjected to autoclave treatment at 121° C. for 15 minutes in 10 mM citrate buffer (pH 6.0), thereby performing an antigen activation treatment.

Thereafter, the tissue array slide was washed with PBS buffer and then subjected to a 1-hour blocking treatment with 1% BSA-containing PBS buffer in a moist chamber. After the blocking treatment, an anti-HER2 rabbit monoclonal antibody (4B5, manufactured by Ventana Medical Systems, Inc.) diluted with 1% BSA-containing PBS buffer to a concentration of 0.05 nM was allowed to react with the tissue section for 2 hours. After washing the tissue section with PBS buffer, the tissue section was further allowed to react for 30 minutes with a biotin-labeled anti-rabbit monoclonal antibody that binds to 4B5 and had been diluted with 1% BSA-containing PBS buffer to a concentration of 2 μg/mL. Thereafter, the melamine-based particles diluted with 1% BSA-containing PBS buffer to a concentration of 0.2 nM were allowed to react with the tissue section for 3 hours under a neutral pH environment (pH 6.9 to 7.4) at room temperature. After this reaction, the tissue array slide was washed with PBS buffer.
(Morphological Staining)

After the immunostaining, hematoxylin-eosin staining (HE staining) was performed. The immunostained section was subjected to hematoxylin staining for 5 minutes with Mayer's hematoxylin solution and then washed with running water of about 45° C. for 3 minutes. Next, after subjecting the section to eosin staining for 5 minutes with 1% eosin solution, an operation of immersing the section in pure ethanol for 5 minutes was repeated four times to perform washing and dehydration. Subsequently, an operation of immersing the section in xylene for 5 minutes was repeated four times to perform clearing. Lastly, the section was mounted with a mounting medium (Entellan New (manufactured by Merck KGaA) to prepare a sample slide for observation.
(Observation)

As described above, a staining solution was produced by dispersing the melamine-based particles in PBS buffer (pH 7.4) at a concentration of 0.2 nM and applied to a tissue array slide, which was subsequently left to stand at room temperature for 2 hours and washed with PBS buffer. Then, the tissue section subjected to the immunostaining and the morphological staining was irradiated with a prescribed excitation light to allow fluorescence to be emitted. The tissue section in this state was observed and photographed under a fluorescence microscope (BX-53, manufactured by Olympus Corporation). Further, bright spots were measured by an ImageJ Find Maxima method.

The excitation light was set to have a wavelength of 575 to 600 nm through an optical filter. In addition, the wavelength range (nm) of the fluorescence to be observed was also set at 612 to 682 nm through an optical filter.

The conditions of the excitation wavelength in the microscope observation and image acquisition were set such that the intensity of the irradiation light in the vicinity of the center of the visual field was 900 W/cm² for excitation at 580 nm. In the image acquisition process, a photograph was taken by arbitrarily setting the exposure time such that the image brightness was not saturated (for example, the exposure time was set at 4,000 µs). Then, the reagent dispersibility, adsorption to cell nuclei and adsorption to the whole tissue were evaluated as described above. The results thereof are shown in Table 2.

Example 2

A case where polystyrene-based particles according to the present invention were produced will now be described. The term "polystyrene-based particles" means resin particles mainly containing polystyrene.

To 5 mL of pure water deaerated by argon bubbling, 0.18 g of glycidyl methacrylate (manufactured by Tokyo Chemical Industry Co., Ltd.), 0.05 g of divinylbenzene, 0.002 g of a fluorescent dye Sulforhodamine 101 (Texas Red dye, manufactured by Sigma-Aldrich) and 0.05 g of 4-aminostyrene (manufactured by Tokyo Chemical Industry Co., Ltd.) were added. After heating the resultant with stirring to 70° C., 0.012 g of a water-soluble azo polymerization initiator, V-50 (manufactured by Wako Pure Chemical Industries, Ltd.), was added and the resulting mixture was allowed to react for 12 hours. This reaction solution was centrifuged at 10,000 G for 20 minutes to recover particles. The recovered particles were purified by dispersing them in pure water and then again centrifuging the resulting dispersion for recovery. The thus obtained particles were added to an excess amount of aqueous ammonia so as to convert the epoxy groups (derived from glycidylmethacrylate) at the particle terminals into amino groups, thereby obtaining Texas Red dye-bound polystyrene nanoparticles having an amino group at a terminal.

The thus obtained dye-bound nanoparticles were adjusted with PBS (phosphate-buffered physiological saline) containing 2 mM of EDTA (ethylenediamine tetraacetic acid) to a concentration of 3 nM. This solution was mixed with SM(PEG)$_4$ (manufactured by Thermo Fisher Scientific K.K.; succinimidyl-[(N-maleimidopropionamido)-tetraethyleneglycol]ester to a final concentration of 10 mM, and the resulting mixture was allowed to react for 1 hour. This mixture was centrifuged at 10,000 G for 20 minutes and the resulting supernatant was removed. Then, PBS containing 2 mM of EDTA was added to disperse the precipitates and the resulting dispersion was centrifuged again. The precipitates were washed three times by the same procedure to obtain dye-embedded nanoparticles having a maleimide group attached to a terminal.

On another front, streptavidin capable of binding to the polystyrene-based particles was obtained in the same manner as in Example 1. The whole amount of this streptavidin and 1 mL of the particles adjusted with PBS containing 2 mM of EDTA to a concentration of 1 nM were mixed and allowed to undergo reaction where these molecules were bound at room temperature for 1 hour. The resultant was then centrifuged and washed with PBS containing 2 mM of EDTA, and only streptavidin-bound polystyrene-based particles (fluorescent nanoparticles) were recovered. Using a zeta potential-measuring device ("Zetasizer Nano", manufactured by Malvern Instruments Ltd.), the zeta potential of the thus recovered polystyrene-based particles in water of pH 7.0 was measured to be −22 mV.

(Immunostaining, Morphological Staining and Observation)

Immunostaining, morphological staining and observation were performed and evaluations of the reagent dispersibility, adsorption to cell nuclei, adsorption to the whole tissue and the like were conducted in the same manner as in Example 1, except that the polystyrene-based particles produced in this Example 2 were used in place of the melamine-based particles of Example 1. The results thereof are shown in Table 2.

Example 3

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of 1,2-bis(2-aminoethoxy)ethane (BAEE, manufactured by Kanto Chemical Co., Ltd.) in place of ethanolamine. The results thereof are shown in Table 2.

Example 4

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of tris(2-aminoethyl)amine (TAEA, manufactured by Kanto Chemical Co., Ltd.) in place of ethanolamine. The results thereof are shown in Table 2.

Example 5

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of 1,2-bis(2-aminoethoxy)ethane (BAEE, manufactured by Kanto Chemical Co., Ltd.) in place of ethanolamine and 16 mg of SM(PEG)$_{24}$ in place of SM(PEG)$_4$. The results thereof are shown in Table 2.

Example 6

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of tris(2-aminoethyl)amine (TAEA, manufactured by Kanto Chemical Co., Ltd.) in place of ethanolamine and 32 mg of SM(PEG)$_{24}$ in place of SM(PEG)$_4$. The results thereof are shown in Table 2. In addition, the photograph observed for the examination of non-specific binding is shown in FIG. 1(D).

Example 7

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of 1,2-bis(2-aminoethoxy)ethane (BAEE, manufactured by Kanto Chemical Co., Ltd.) in place of ethanolamine and 16 mg of SM(PEG)$_{12}$ in place of SM(PEG)$_4$. The results thereof are shown in Table 2. In addition, the photograph observed for the examination of non-specific binding is shown in FIG. 1(C).

Example 8

Immunostaining, morphological staining and observation were performed and evaluations of the reagent dispersibility, adsorption to cell nuclei and adsorption to the whole tissue were conducted in the same manner as in Example 1, except that melamine-based particles (fluorescent nanoparticles) were produced using 20 µL of 1,2-bis(2-aminoethoxy)ethane (BAEE, manufactured by Kanto Chemical Co., Ltd.) in place of ethanolamine and 3 mg of SM(PEG)$_2$ in place of SM(PEG)$_4$. The results thereof are shown in Table 2.

Example 9

Immunostaining, morphological staining and observation were performed and evaluations of the reagent dispersibility, adsorption to cell nuclei, adsorption to the whole tissue and the like were conducted in the same manner as in Example 1, except that melamine-based particles (fluorescent nanoparticles) were produced using 20 µL of 1,2-bis(2-aminoethoxy)ethane (BAEE, manufactured by Kanto Chemical Co., Ltd.) in place of ethanolamine and 59 mg of SM(PEG)$_{44}$ in place of SM(PEG)$_4$. The results thereof are shown in Table 2.

Example 10

Production of melamine-based particles (fluorescent nanoparticles), immunostaining, morphological staining and observation were performed and evaluations of the reagent dispersibility, adsorption to cell nuclei and adsorption to the whole tissue were conducted in the same manner as in Example 1, except that melamine-based particles were produced at an average particle size of 28 nm using 20 µL of tris(2-aminoethyl)amine (TAEA, manufactured by Kanto Chemical Co., Ltd.) in place of ethanolamine and 32 mg of SM(PEG)$_{24}$ in place of SM(PEG)$_4$. The results thereof are shown in Table 2.

Example 11

Production of melamine-based particles (fluorescent nanoparticles), immunostaining, morphological staining and observation were performed and evaluations of the reagent dispersibility, adsorption to cell nuclei and adsorption to the whole tissue were conducted in the same manner as in Example 1, except that melamine-based particles were produced at an average particle size of 310 nm using 20 µL of tris(2-aminoethyl)amine (TAEA, manufactured by Kanto Chemical Co., Ltd.) in place of ethanolamine and 32 mg of SM(PEG)$_{24}$ in place of SM(PEG)$_4$. The results thereof are shown in Table 2.

Comparative Example 1

Immunostaining, morphological staining and observation were performed and evaluations of the reagent dispersibility, adsorption to cell nuclei and adsorption to the whole tissue were conducted in the same manner as in Example 1, except that melamine-based particles were produced by directly binding streptavidin to the dye resin particles without amino group introduction by ethanolamine and PEG addition by SM(PEG)$_4$. The results thereof are shown in Table 2. In addition, the photograph observed for the examination of non-specific binding is shown in FIG. 1(A).

The direct bonding of streptavidin to the melamine-based particles immediately after polymerization was performed by the following method.

A suspension containing 10% of melamine particles (=100 mg of solids) is measured in a volume of 1 mL, placed in an Eppendorf cap and suspended in 1 mL of 50 mM MES buffer (2-morpholine ethanesulfonic acid (Merck KGaA), pH 5.5), and the resultant is subsequently centrifuged at 60,000 rpm using an ultracentrifuge. The resulting supernatant is discarded and washing operation is repeated. Next, the particles are resuspended in 1 mL of MES buffer and transferred to a sealable glass tube. Then, 100 µL of an EDC/NHS solution (MES buffer containing 100 mg/mL of EDC and 16 mg/mL of N-hydroxysuccinimide (Merck KGaA)) is added. The suspended state of the melamine particles is maintained with rotation at room temperature for 1 hour. During this period, NHS is coupled with carboxyl groups on the particle surfaces. This sample is recentrifuged and the resulting supernatant is discarded. The mixture is washed again with 1 mL of MES buffer. The particles are resuspended in 1 mL of a protein (streptavidin) solution and the resulting suspension is maintained under rotation overnight at room temperature. The corresponding sample is resuspended in 1 mL of MES buffer (without addition of the EDC/NHS and protein solutions) and the resulting suspension is maintained under rotation overnight at room temperature. After centrifuging the sample and adding thereto 1 ml of an ethanolamine solution, this sample is further subjected to rotation for 1 hour and recentrifuged. Ethanolamine reacts with residual activated ester to generate an amide. Then, the mixture is washed three times with 1 ml of PBS buffer each time. Lastly, the particles are resuspended in PBS buffer to make the particles storable in a refrigerator at 4° C.

Comparative Example 2

Immunostaining, morphological staining and observation were performed and evaluations of the reagent dispersibility, adsorption to cell nuclei, adsorption to the whole tissue and the like were conducted in the same manner as in Example 1, except that the amino group addition was performed using 20 µL of 3-aminopropyltriethoxysilane (APS) was used in place of ethanolamine and that 16 mg of SM(PEG)$_{12}$ was used in place of SM(PEG)$_4$. The results thereof are shown in Table 2.

It is noted here that APS (H$_2$N—C$_3$H$_6$—Si(OC$_2$H$_5$)$_3$) was used to reduce the zeta potential of the melamine-based particles; and that reactive silanol groups (—SiOH) generated by hydrolysis of the ethoxy groups of the APS molecules react with the amino groups of the melamine-based particles and the APS molecules are thereby added to the melamine-based particles.

Comparative Example 3

Immunostaining, morphological staining and observation were performed and evaluations of the reagent dispersibility, adsorption to cell nuclei and adsorption to the whole tissue were conducted in the same manner as in Example 1, except that 20 µL of 3-aminopropyltriethoxysilane (APS) and 4 µL of tetraethoxysilane (TEOS) were added in place of ethanolamine and that 16 mg of SM(PEG)$_{12}$ was used in place of SM(PEG)$_4$. The results thereof are shown in Table 2.

It is noted here that TEOS (Si(OC$_2$H$_5$)$_4$) added along with TEOS was used to reduce the zeta potential of the melamine-based particles; and that reactive silanol groups (—SiOH) generated by hydrolysis of the ethoxy groups of the TEOS molecules react with the amino groups of the melamine-based particles and the TEOS molecules are thereby added to the melamine-based particles.

(Discussion)

In a neutral pH environment (pH 6.9 to 7.4) which is the pH environment where the immunostaining was performed, by changing the selection of the amino group-introducing compound, such as ethanolamine, TAEA or BAEE that chemically modifies the surfaces of the resin particles, as well as the chain length of PEG that performs chemical modification in the same manner, the zeta potential of the fluorescent nanoparticles of the melamine-based or polystyrene-based particles in water of pH 7.0 was set to be −14 mV to −60 mV. Then by dispersing the particles in a pH 7.4 buffer and using the resultant as a staining solution, only the specific binding between streptavidin and biotin (biomolecular recognition) was allowed to occur while non-specific binding of the fluorescent nanoparticles to the biomolecules in the cells was suppressed (see Table 1 and FIG. 1). This consequently made it possible to specifically stain only the biomolecules to be stained in the cells (see FIG. 1 for comparison between Examples 6 or 7 and Comparative Example 1).

TABLE 2

| | Particle constitution (*1) | Zeta potential | Reagent dispersibility (*2) | Adsorption to cell nuclei (*3) Particle concentration (nM) | | Adsorption to whole tissue (*4) | Elution of dye (*5) | Average number of cell bright spots (Evaluation)*6 |
|---|---|---|---|---|---|---|---|---|
| | | | | 0.2 | 0.005 | | | |
| Comparative Example 1 | melamine-based particles (150 nm) + SA | 28 mV | ○ | x | x | ○ | ○ | not measurable because the bright spots could not be separated from each other due to a large amount of adsorption |
| Comparative Example 2 | melamine-based particles (150 nm) + PEG12 (APS) + SA | −6 mV | x | x | ○ | ○ | ○ | not measurable because the bright spots could not be separated from each other due to a large amount of adsorption |
| Comparative Example 3 | melamine-based particles (150 nm) + PEG12 (APS + TEOS) + SA | −66 mV | ○ | ○ | ○ | x | 0 | not measurable because the bright spots could not be separated from each other due to a large amount of adsorption |
| Example 1 | melamine-based particles (150 nm) + PEG4 (ethanolamine) + SA | −14 mV | ○ | ○ | ○ | ○ | ○ | 14 (Δ) |
| Example 2 | polystyrene-based particles (100 nm) + PEG4 (BAEE) + SA | −22 mV | ○ | ○ | ○ | ○ | x | 34 (○*7) |
| Example 3 | melamine-based particles (150 nm) + PEG4 (BAEE) + SA | −23 mV | ○ | ○ | ○ | ○ | ○ | 38 (○) |
| Example 4 | melamine-based particles (150 nm) + PEG4 (TAEA) + SA | −22 mV | ○ | ○ | ○ | ○ | ○ | 36 (○) |
| Example 5 | melamine-based particles (150 nm) + PEG24 (BAEE) + SA | −33 mV | ○ | ○ | ○ | ○ | ○ | 39 (○) |
| Example 6 | melamine-based particles (150 nm) + PEG24 (TAEA) + SA | −38 mV | ○ | ○ | ○ | ○ | ○ | 34 (○) |
| Example 7 | melamine-based particles (150 nm) + PEG12 (BAEE) + SA | −48 mV | ○ | ○ | ○ | ○ | ○ | 42 (○) |
| Example 8 | melamine-based particles (150 nm) + PEG2 (BAEE) + SA | −28 mV | ○ | ○ | ○ | ○ | ○ | 13 (Δ) |
| Example 9 | melamine-based particles (150 nm) + PEG44 (BAEE) + SA | −58 mV | ○ | ○ | ○ | ○ | ○ | 18 (Δ) |
| Example 10 | melamine-based particles (28 nm) + PEG24 (TAEA) + SA | −23 mV | ○ | ○ | ○ | ○ | ○ | not measurable, only the brightness was measurable (Δ) |
| Example 11 | melamine-based particles (310 nm) + PEG24 (TAEA) + SA | −28 mV | ○ | ○ | ○ | ○ | ○ | 9 (Δ) |

APS: 3-aminopropyltriethoxysilane,
PEG: polyethylene glycol,
TEOS: tetraethoxysilane,
BAEE: 1,2-bis(2-aminoethoxy)ethane,
SA: streptavidin,
TAEA: tris(2-aminoethyl)amine
(*1) The length shown in parentheses under "Particle constitution" indicates the average particle size of the fluorescent nanoparticles.
(*2) Precipitation after 1-day storage: present "x", absent = "○"
(*3) Average number of bright spots per cell nucleus: "x" = 1 or more, "○" = less than 1
(*4) Average number of bright spots per cell: "x" = 1 or more, "○" = less than 1
(*5) Bleeding of fluorescent dye during observation: "x" = present, "○" = absent
*6Average number of bright spots per cell measured for 60 cells
*7Observation was made in an aqueous mounting medium.

Example 13

The zeta potential of the melamine-based particles prepared in Example 7 was measured to be −6.7 mV in a state of being dispersed in PBS (pH 7.4) at a concentration of 2 mg/mL. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3. The results thereof are shown in Table 3.

Example 14

The zeta potential of the melamine-based particles prepared in Example 7 was measured to be −7.8 mV in a state of being dispersed in a Dako dilution (manufactured by Dako Japan Co., Ltd.; "Antibody Diluent, Background Reducing", product number: S3022) (pH 7.8) at a concentration of 2 mg/mL. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 15

The zeta potential of the melamine-based particles prepared in Example 7 was measured to be −7.3 mV in a state of being dispersed in PBS (pH 7.2) containing 1% by weight of BSA at a concentration of 2 mg/mL. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 16

The zeta potential of the melamine-based particles prepared in Example 7 was measured to be −7.0 mV in a state of being dispersed in PBS (pH 7.1) containing 5% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 17

The zeta potential of the melamine-based particles prepared in Example 7 was measured to be −6.6 mV in a state of being dispersed in PBS (pH 7.0) containing 10% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 18

The zeta potential of the melamine-based particles prepared in Example 7 was measured to be −4.6 mV in a state of being dispersed in PBS (pH 7.0) containing 20% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 19

The zeta potential of the melamine-based particles prepared in Example 7 was measured to be −2.4 mV in a state of being dispersed in PBS (pH 7.3) containing 1% by weight of BSA, 0.1% by weight of Tween 20 (registered trademark) and 0.015 N of sodium azide (NaN$_3$) as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 20

The zeta potential of the melamine-based particles prepared in Example 7 was measured to be −2.0 mV in a state of being dispersed in PBS (pH 7.2) containing 5% by weight of BSA, 0.1% of Tween 20 (registered trademark) and 0.015 N of NaN$_3$ as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 21

The zeta potential of the melamine-based particles prepared in Example 7 was measured to be −2.2 mV in a state of being dispersed in PBS (pH 7.2) containing 10% by weight of BSA, 0.1% by weight of Tween 20 (registered trademark) and 0.015N of NaN$_3$ as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 22

The zeta potential of the melamine-based particles prepared in Example 7 was measured to be −9.6 mV in a state of being dispersed in 50 mM Tris-HCl (pH 7.5) containing 10% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 23

The zeta potential of the melamine-based particles prepared in Example 7 was measured to be −7.6 mV in a state of being dispersed in 50 mM Tris-HCl (pH 7.5) containing 10% by weight of BSA, 0.1% by weight of Tween 20 (registered trademark) and 0.015 N of $NaN_3$ as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 24

The zeta potential of the melamine-based particles prepared in Example 7 was measured to be −6.9 mV in a state of being dispersed in a 50 mM phosphate buffer (pH 6.2) containing 1% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 25

The zeta potential of the melamine-based particles prepared in Example 7 was measured to be −6.6 mV in a state of being dispersed in a 50 mM phosphate buffer (pH 6.1) containing 5% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

Example 26

The zeta potential of the melamine-based particles prepared in Example 7 was measured to be −6.5 mV in a state of being dispersed in a 50 mM phosphate buffer (pH 6.0) containing 10% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 3.

TABLE 3

| Example | Particle constitution (*1) | Buffer | Additive | Zeta potential of fluorescent nanoparticles in buffer | Reagent dispersibility (*2) | Adsorption to cell nuclei (*3) concentration (nM) 0.2 | 0.005 | Adsorption to whole tissue (*4) | Buffer pH | Elution of dye (*5) | Presence/absence of bright spot (0 = present, x = absent) |
|---|---|---|---|---|---|---|---|---|---|---|---|
| Example 13 | melamine-based particles (150 nm) + PEG12 (BAEE) + SA | PBS | — | −6.7 mV | ○ | ○ | ○ | ○ | 7.4 | ○ | ○ |
| Example 14 | | Dako dilution | — | −7.8 mV | ○ | ○ | ○ | ○ | 7.8 | ○ | ○ |
| Example 15 | | PBS | 1% BSA | −7.3 mV | ○ | ○ | ○ | ○ | 7.2 | ○ | ○ |
| Example 16 | | PBS | 5% BSA | −7.0 mV | ○ | ○ | ○ | ○ | 7.1 | ○ | ○ |
| Example 17 | | PBS | 10% BSA | −6.6 mV | ○ | ○ | ○ | ○ | 7.0 | ○ | ○ |
| Example 18 | | PBS | 20% BSA | −4.6 mV | ○ | ○ | ○ | ○ | 7.0 | ○ | ○ |
| Example 19 | | PBS | 1% BSA 0.1% Tween 20 0.015N $NaN_3$ | −2.4 mV | ○ | ○ | ○ | ○ | 7.3 | ○ | ○ |
| Example 20 | | PBS | 5% BSA 0.1% Tween 20 0.015N $NaN_3$ | −2.0 mV | ○ | ○ | ○ | ○ | 7.2 | ○ | ○ |
| Example 21 | | PBS | 10% BSA 0.1% Tween 20 0.015N $NaN_3$ | −2.2 mV | ○ | ○ | ○ | ○ | 7.2 | ○ | ○ |
| Example 22 | | Tris-HCl | 10% BSA | −9.6 mV | ○ | ○ | ○ | ○ | 7.5 | ○ | ○ |
| Example 23 | | Tris-HCl | 10% BSA 0.1% Tween 20 0.015N $NaN_3$ | −7.6 mV | ○ | ○ | ○ | ○ | 7.1 | ○ | ○ |
| Example 24 | | phosphate | 1% BSA | −6.9 mV | ○ | ○ | ○ | ○ | 6.2 | ○ | ○ |
| Example 25 | | phosphate | 5% BSA | −6.6 mV | ○ | ○ | ○ | ○ | 6.1 | ○ | ○ |
| Example 26 | | phosphate | 10% BSA | −6.5 mV | ○ | ○ | ○ | ○ | 6.0 | ○ | ○ |

Comparative Example 4

The zeta potential of the melamine-based particles prepared in Example 7 was measured to be −12.2 mV in a state of being dispersed in 50 mM Tris-HCl (pH 7.8). Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 5

The zeta potential of the melamine-based particles prepared in Example 7 was measured to be −12.6 mV in a state of being dispersed in 50 mM Tris-HCl (pH 7.8) containing 1% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 6

The zeta potential of the melamine-based particles prepared in Example 7 was measured to be −11.9 mV in a state of being dispersed in 50 mM Tris-HCl (pH 7.6) containing 5% by weight of BSA. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 7

The zeta potential of the melamine-based particles prepared in Example 7 was measured to be −14.0 mV in a state of being dispersed in 50 mM Tris-HCl (pH 7.5) containing 1% by weight of BSA, 0.1% by weight of Tween 20 (registered trademark) and 0.015 N of $NaN_3$ as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 8

The zeta potential of the melamine-based particles prepared in Example 7 was measured to be −10.1 mV in a state of being dispersed in 50 mM Tris-HCl (pH 7.2) containing 5% by weight of BSA, 0.1% by weight of Tween 20 (registered trademark) and 0.015 N of $NaN_3$ as components. Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 9

The zeta potential of the melamine-based particles prepared in Example 7 was measured to be −28.2 mV in a state of being dispersed in 50 mM Tris-HCl (pH 5.2) containing 0.1% by weight of Tween 20 (registered trademark). Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 10

The zeta potential of the melamine-based particles prepared in Example 7 was measured to be −32.2 mV in a state of being dispersed in a 50 mM Tris-HCl buffer (pH 5.8) containing 0.1% by weight of DISPER BYK-2010 (registered trademark) (manufactured by BYK Japan K.K.). Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

Comparative Example 11

The zeta potential of the melamine-based particles prepared in Example 7 was measured to be −27.7 mV in a state of being dispersed in a 50 mM Tris-HCl buffer (pH 5.4) containing 0.1% by weight of DISPER BYK-2015 (registered trademark) (manufactured by BYK Japan K.K.). Staining solutions were each produced by adjusting the concentration of the melamine-based particles in this dispersion to be 0.2 nM or 0.005 nM, and confirmation of non-specific binding, immunostaining, morphological staining, observation and the like were performed in the same manner as in Example 1. The results thereof are shown in Table 4.

TABLE 4

| Example | Particle constitution | Buffer | Additive | Zeta potential of fluorescent nanoparticles in buffer | Reagent dispersibility (*2) | Adsorption to cell nuclei (*3) Particle concentration (nM) 0.2 | Adsorption to cell nuclei (*3) Particle concentration (nM) 0.005 | Adsorption to whole tissue (*4) | Buffer pH | Elution of dye (*5) | Presence/absence of bright spot (○ = present, x = absent) |
|---|---|---|---|---|---|---|---|---|---|---|---|
| Comparative Example 4 | melamine-based particles (150 nm) + PEG12 (BAEE) + SA | Tris-HCl | — | −12.2 mV | ○ | ○ | ○ | ○ | 7.8 | ○ | x |
| Comparative Example 5 | | Tris-HCl | 1% BSA | −12.6 mV | ○ | ○ | ○ | ○ | 7.8 | ○ | x |
| Comparative Example 6 | | Tris-HCl | 5% BSA | −11.9 mV | ○ | ○ | ○ | ○ | 7.6 | ○ | x |
| Comparative Example 7 | | Tris-HCl | 1% BSA 0.1% Tween 20 0.015N NaN$_3$ | −14.0 mV | ○ | ○ | ○ | ○ | 7.5 | ○ | x |
| Comparative Example 8 | | Tris-HCl | 5% BSA 0.1% Tween 20 0.015N NaN$_3$ | −10.1 mV | ○ | ○ | ○ | ○ | 7.2 | ○ | x |
| Comparative Example 9 | | Tris-HCl | 0.1% Tween 20 | −28.2 mV | ○ | ○ | ○ | ○ | 5.2 | ○ | x |
| Comparative Example 10 | | Tris-HCl | 0.1% DISPER BYK-2010 | −32.2 mV | ○ | ○ | ○ | ○ | 5.8 | ○ | x |
| Comparative Example 11 | | Tris-HCl | 0.1% DISPER BYK-2015 | −27.7 mV | ○ | ○ | ○ | ○ | 5.4 | ○ | x |

(Results and Discussion)

By dispersing the melamine-based particles prepared in Example 7 into a PBS buffer of pH 6.0 to 8.0 and controlling the zeta potential of the melamine-based particles in this pH buffer at 0 mV to −10 mV, not only excellent reagent dispersibility of the melamine-based particles was attained but also non-specific adsorption of the melamine-based particles to cell nuclei and whole tissue was suppressed, so that the average number of cell bright spots was evaluated as "○" for all items (Example 13). Even with an addition of a component(s) affecting the zeta potential value such as BSA and Tween 20 (registered trademark), as long as the zeta potential of the melamine-based particles in each buffer was kept within the above-described range, the same effects were obtained (Examples 15 to 21). In addition, even when the PBS buffer was changed to a Dako dilution, Tris-HCl or phosphate buffer, the same effects were also obtained (Examples 14 and 22 to 26) as long as the zeta potential of the melamine-based particles in each buffer was kept within the above-described range.

Further, when Tris-HCl with buffering capacity was used and the zeta potential of the melamine-based particles in the buffer was not in the range of 0 mV to −10 mV, bright spots were not obtained (Comparative Examples 4 to 11).

From these results, in order to obtain bright spots, it is believed necessary to use a solution prepared by dispersing melamine-based particles in a buffer of pH 6.0 to 8.0, wherein the zeta potential of the melamine-based particles in the buffer is 0 mV to −10 mV, as a staining solution. Moreover, this can also be understood from the results that, also for those melamine-based particles of Example 1 to 6 and 8 to 11 that had different particle constitutions from that of Example 7 (see Table 2) as described above, bright spots were obtained by staining with a staining solution prepared by dispersing the melamine-based particles in a PBS buffer (pH 7.4) as in Example 13 (see Table 2).

Thus far, embodiments and examples of the present invention have been described referring to the drawings; however, the present invention is not restricted to these embodiments and examples, and design modifications and the like can be made as long as they do not deviate from the gist of the present invention.

The invention claimed is:

1. Fluorescent nanoparticles for fluorescently staining a target substance, said target substance comprising a portion to be stained, and said fluorescent nanoparticles comprising:
   dye resin particles having a fluorescent dye;
   an amino group-containing compound bound to said dye resin particles;
   a PEG bound to the amino group-containing compound, the PEG having 4 to 24 oxyethylene units (—CH$_2$CH$_2$—O—); and
   a moiety bound to the PEG, the moiety capable of binding to said portion to be stained of said target substance,
   wherein said fluorescent nanoparticles have a zeta potential of −10 mV to −60 mV in water of pH 7.0, and
   said amino group-containing compound has two or more free amino groups when bound to said dye resin particles.

2. The fluorescent nanoparticles according to claim 1, wherein said amino group-containing compound is 1,2-bis(2-aminoethoxy)ethane (BAEE) or tris(2-aminoethyl)amine (TAEA).

3. The fluorescent nanoparticles according to claim 1, wherein the resin of said dye resin particles is a melamine resin.

4. The fluorescent nanoparticles according to claim 3, wherein said moiety is streptavidin obtained through a reaction with N-succinimidyl-S-acetylthioacetate (SATA) or 2-iminothiolane.

5. The fluorescent nanoparticles according to claim 1, wherein said staining is immunostaining.

6. A staining solution comprising the fluorescent-nanoparticles according to claim 1 dispersed in a buffer.

7. The staining solution according to claim 6, further comprising at least one of a protein or a surfactant.

8. The fluorescent nanoparticles according to claim 1, having an average particle size of not smaller than 40 nm and not larger than 200 nm.

9. A method of producing the fluorescent nanoparticles recited in claim 1,
   said method comprising the step of chemically modifying the surfaces of dye resin particles comprising a fluorescent dye embedded therein or immobilized thereon so as to impart said dye resin particles with a zeta potential that allows the resulting fluorescent nanoparticles as a whole to have a zeta potential of −10 mV to −60 mV in water of pH 7.0.

* * * * *